United States Patent [19]

Skotnikov et al.

[11] Patent Number: 5,741,983
[45] Date of Patent: Apr. 21, 1998

[54] SOIL SAMPLER FOR ANALYSIS FOR FERTILIZER DETERMINATION

[75] Inventors: Andrey V. Skotnikov; Vladimir Pisarchik; Gennady Valjushkevich, all of Minsk, Belarus

[73] Assignee: Iboco, Inc., Benson, Minn.

[21] Appl. No.: 610,568

[22] Filed: Mar. 8, 1996

Related U.S. Application Data

[63] Continuation of Ser. No. 286,769, Aug. 5, 1994, abandoned.

[30] Foreign Application Priority Data

Aug. 5, 1993 [BY] Belarus ................................. 00600-01

[51] Int. Cl.$^6$ ..................................................... G01N 1/08
[52] U.S. Cl. ..................... 73/864.45; 73/864.44; 175/20
[58] Field of Search ............................ 73/864.44, 864.45, 73/863.01, 864.41, 864.42, 864.43; 172/21, 22; 175/58, 20

[56] References Cited

U.S. PATENT DOCUMENTS

| Re. 30,901 | 4/1982 | Boxrud | 73/864.45 |
|---|---|---|---|
| 3,415,363 | 12/1968 | Horeth et al. | 73/864.91 |
| 3,468,379 | 9/1969 | Rushing et al. | 172/2 |
| 3,625,296 | 12/1971 | Mabry | 73/864.41 |
| 4,358,054 | 11/1982 | Ehrat | 239/155 |
| 4,588,127 | 5/1986 | Ehrat | 239/156 |
| 4,630,773 | 12/1986 | Ortlip | 239/1 |
| 4,714,196 | 12/1987 | McEachern et al. | 239/62 |
| 4,869,115 | 9/1989 | Edwards et al. | 73/864.41 |
| 5,033,397 | 7/1991 | Colburn, Jr. | 111/118 |
| 5,050,771 | 9/1991 | Hanson et al. | 222/1 |
| 5,220,876 | 6/1993 | Monson et al. | 111/130 |
| 5,339,700 | 8/1994 | Wright et al. | 73/864.34 |
| 5,394,949 | 3/1995 | Wright et al. | 175/20 |
| 5,419,211 | 5/1995 | Rodel et al. | 73/864.45 |

FOREIGN PATENT DOCUMENTS

| 3612409 | 10/1987 | Germany | 73/864.41 |
|---|---|---|---|
| 1682857 | 10/1991 | U.S.S.R. | 73/864.41 |

OTHER PUBLICATIONS

*Using a Multifactor System to Develop Crop Production Recommendations*, by John L. Strauss, Taralon Corporation, Jul. 27–28, 1976, pp. 73–77.

*Blending System Able to Apply Eight Products Simultaneously*, "Outstanding Innovations for 1993" The Agricultural Engineering 50 1993.

Translation DE 3612409.

Primary Examiner—Hezron E. Williams
Assistant Examiner—Nashmiya Ashraf
Attorney, Agent, or Firm—Westman, Champlin & Kelly, P.A.

[57] ABSTRACT

An automatic soil sampler (10) removes soil samples (65) at known locations and transfers the samples to a packaging station (23) where the samples are packaged and identified. The packages (87) are left in a strip and moved to a container (168). The sampler (10) repeats the sampling function at identifiable intervals measured by an odometer (11A) and permits the sampling and packaging to be completed rapidly.

15 Claims, 18 Drawing Sheets

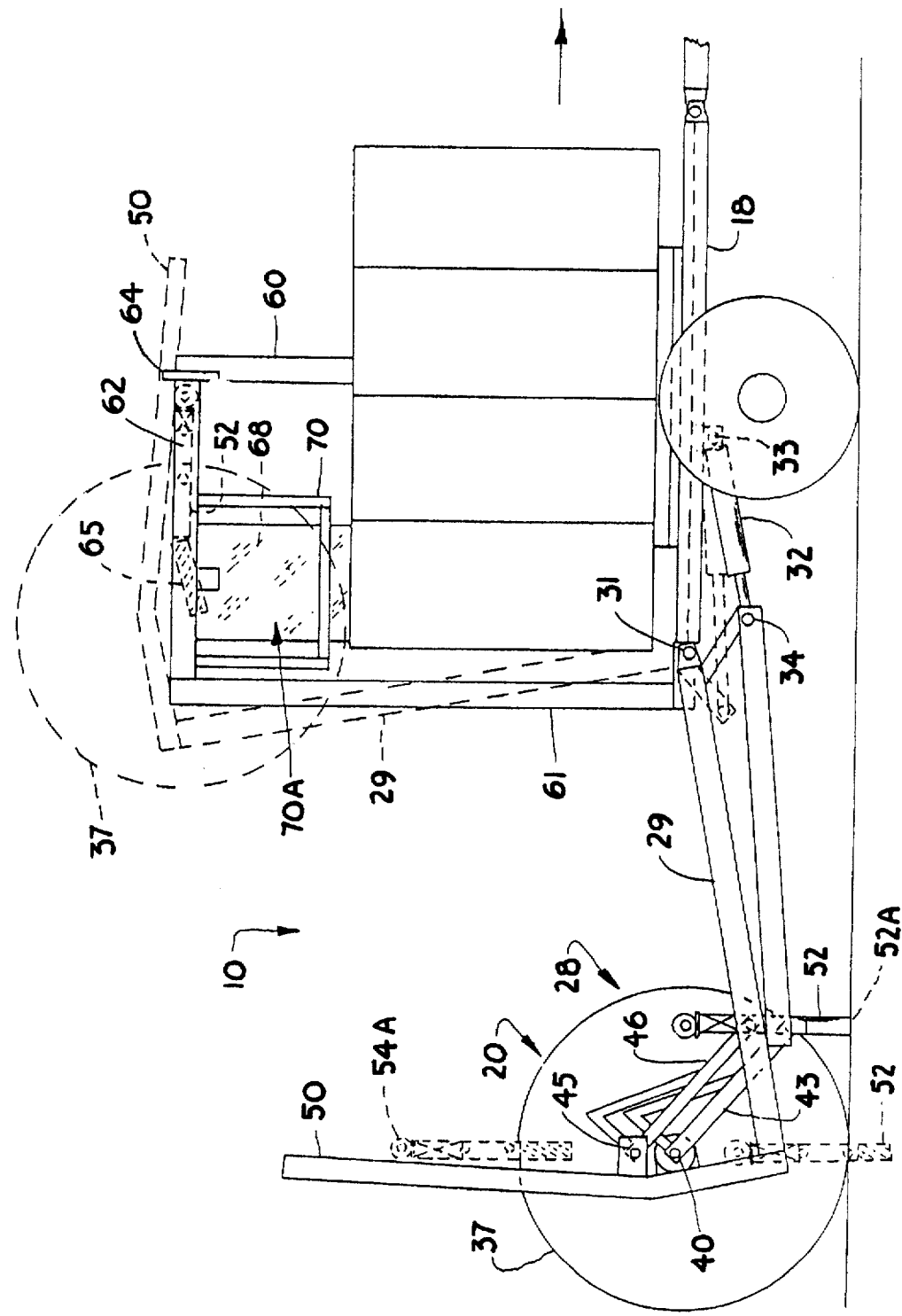

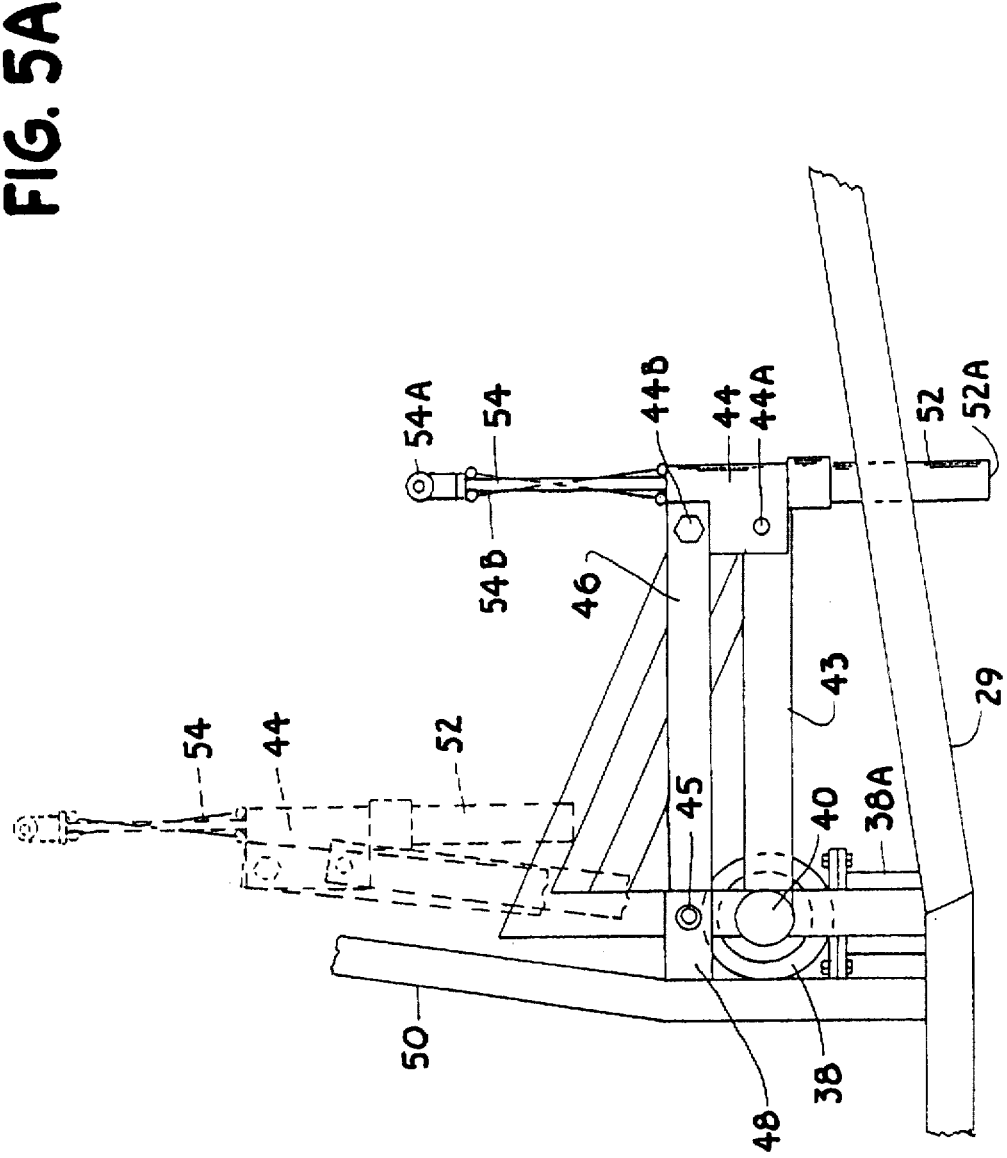

SOIL SAMPLER FOR ANALYSIS FOR FERTILIZER DETERMINATION

This is a continuation of application Ser. No. 08/286,769, filed Aug. 5, 1994 now abandoned.

BACKGROUND OF THE INVENTION

The present invention relates to determine needs for fertilizer application on agriculture lands.

Each field for growing crops is known to contain several soil types, which may be classified according to relative content of sand, clay and humus. There are several common soil types requiring different specific fertilizer for optimum production. Usually, each field contains various soil types placing different requirements in the different areas.

The most common practice is to fertilize the whole field according to the demand of the poorest soils, or according to the demand of average soils, leading to the fact that many field areas receive more or less fertilizer than optimum. This leads to a loss of excess fertilizer and potential lowering crop yield in the whole area compared to optimum ones.

There is a need for economical methods and apparatus to apply fertilizers according to the demand of specific areas in a field.

The prior art discloses methods for fertilizer application based on unification of soil types being determined from IR photography or soil maps and administration of the predetermined rate of fertilizer application for the soil types.

However, even in the determined soil type, for instance, "light loam", the amount of clay and powder-like sand may vary in quite a wide range, not speaking of loam unification. It is also worthy to note the amount of irreversible coupled fertilizer that is inaccessible for plants, will be dependent on the content of salts, clay and powder-like sand and humus in each specific place of the field. Therefore, to apply fertilizer accurately, it is necessary to determine the fertility of the soil in small regions of each field to provide accurate information about content of nutrients and micro elements in a given area forming a grid of the field. Obtaining soil samples over a small spaced grid, by frequent sampling in an identified grid for a specific field permits analyzing the soil with sufficient frequency and accuracy to provide information about fertilizers to be applied.

The above-mentioned object is implemented by preparing a program of applying fertilizer, seed sowing or both, irrespective of the machine used, by means of composing a field map according to the motion pattern, subsequent soil sampling at known locations on the field intervals determined by the device, marking the samples as to the location where they were taken and analyzing physical and mechanical properties with subsequent determining the necessary level of fertilizer application for each soil sample. The needed fertilizer is then applied.

SUMMARY OF THE INVENTION

The present invention relates to a method and apparatus for improving the accuracy of the application of fertilizer in local, small regions of a given agricultural field. An apparatus is disclosed for obtaining soil samples in preselected, identified, small field areas for subsequent laboratory analysis, and from the analysis determination of the type and amount of fertilizer to be applied in each of the small areas.

An agricultural field is sampled in a "grid" pattern by operating a probe that removes a core of earth, and deposits it into a bagging apparatus where it is sealed and identified as to a particular grid location from which it was obtained. The sample is then transported to a laboratory for analysis, and the soil fertility is determined so that the amount of fertilizer needed is determined, taking into account several factors including the amount of particular types of fertilizer elements that are unobtainable by plants from the soil. The fertilizer is then applied in that particular grid section by either following the path taken by the soil sampler or by separate navigation. The machine includes a plurality of bins that can be filled with the packaged soil samples, and each bin can be removed as a unit. The appropriate identification is placed on each of the samples. The packaged soil samples are removed to a laboratory station where they are analyzed, and the soil fertility is determined for each individual area forming the grid in the field. This information is then utilized for appropriately establishing a grid map of the field based on needs of fertilizers to be applied which can be put into an on-board computer on a fertilizing apparatus, and upon proper location by retracing the path of the sampler or by navigation, such as GPS navigation, so that it is known that the fertilizer applicator is in a particular grid section, and the exact amount and type of fertilizer can be applied in each section.

The fertilizer applicator will generally follow the path or very close to the same path as the soil sampler, and the position of the fertilizer applicator can be determined on the basis of x-y coordinates for the grid, which would be used for identification of the soil sample throughout its packaging and analysis steps.

Additionally, the lines along which the sampling is taking place can be marked in a suitable manner by either digging a small furrow along side the line of sampling, or putting a spray paint trace on the ground so that the subsequent fertilizer application can follow the center line path of the prime mover moving the soil sampler. The method includes trying the soil sampling, soil analysis, and fertilizer application together.

BRIEF DESCRIPTION OF THE DRAWINGS

FIG. 5 is a further detailed side view of the automatic soil sampler;

FIG. 5A is an enlarged side view of a soil sampling probe assembly;

DETAILED DESCRIPTION OF THE PREFERRED EMBODIMENTS

Figure 1:
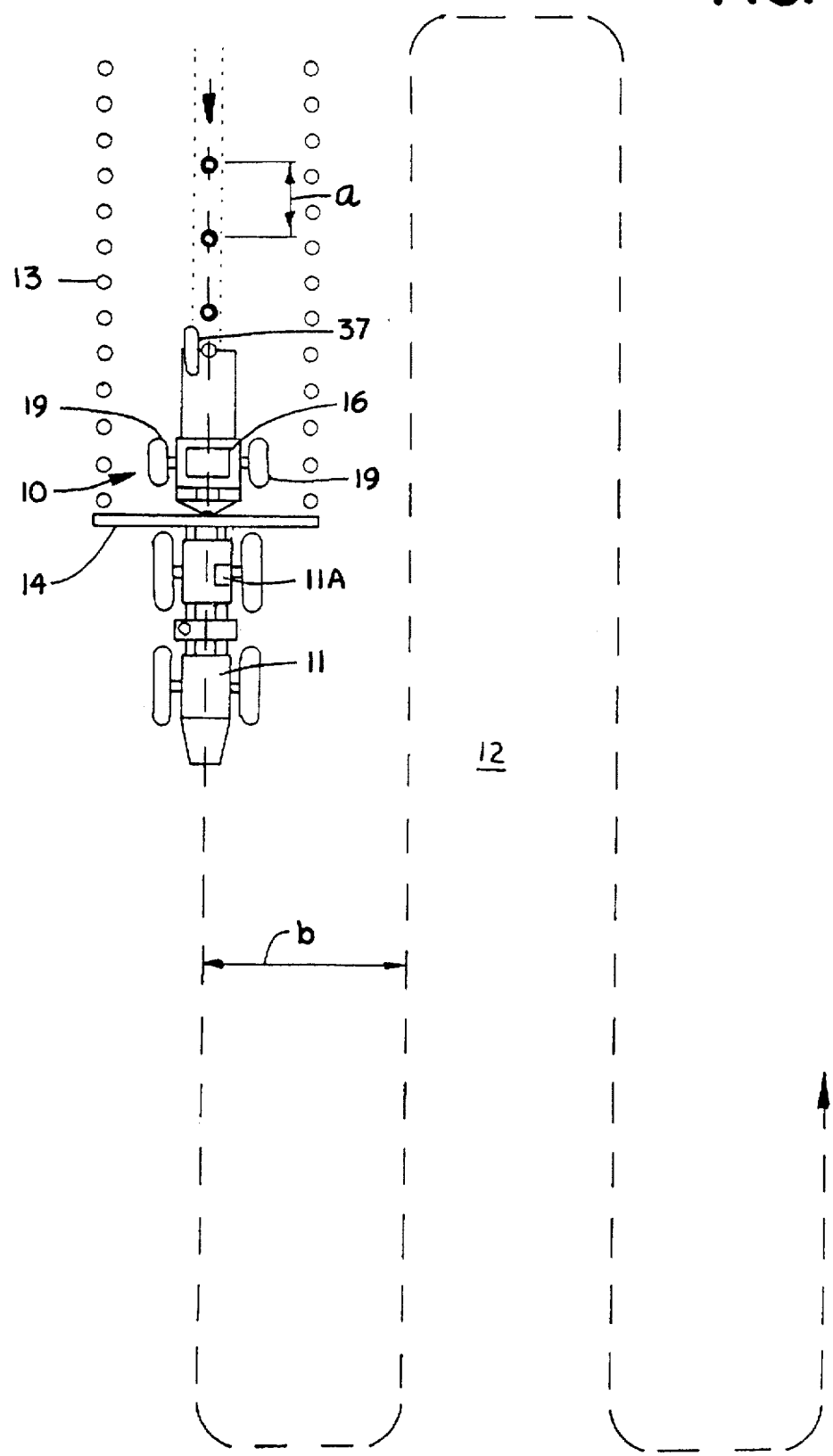
FIG. 1 is a schematic representation of a soil sampling system used to establish a grid pattern.

FIG. 1 schematically illustrates an automatic soil sampler 10 moving over a field 12 in a back and forth motion pattern used by a fertilizer spreader, and providing a series of samples of soil at selected spacing (10–15 meters) along each path to provide samples across a field in a grid. The data on the grid spacing and sampling depth are entered into a memory that also provides an x-y location of each sample taken for identification. The sample depth can be preset by suitable adjustments prior to sampling.

The grid spacing is determined by the parameters "a" and "b" where "a" is distance between adjacent samples, and "b" is the coverage width of a fertilizer spreader again perhaps 10–15 meters.

To determine the grid spacing for the map, a marker with a distance sensor or other navigation means may be used in a known manner. GPS navigation permits accurate x-y coordinates or an odometer 11A (such as a radar odometer) on a towing vehicle 11 can give the "y" distance from a start signal that can be given by an operator at the start of each pass down the field from each end. The "x" distance shown at "b" may be established by foam markers 13 which are correlated to a start position in the field and give the lateral offset of each pass of the sampler.

Figure 2:
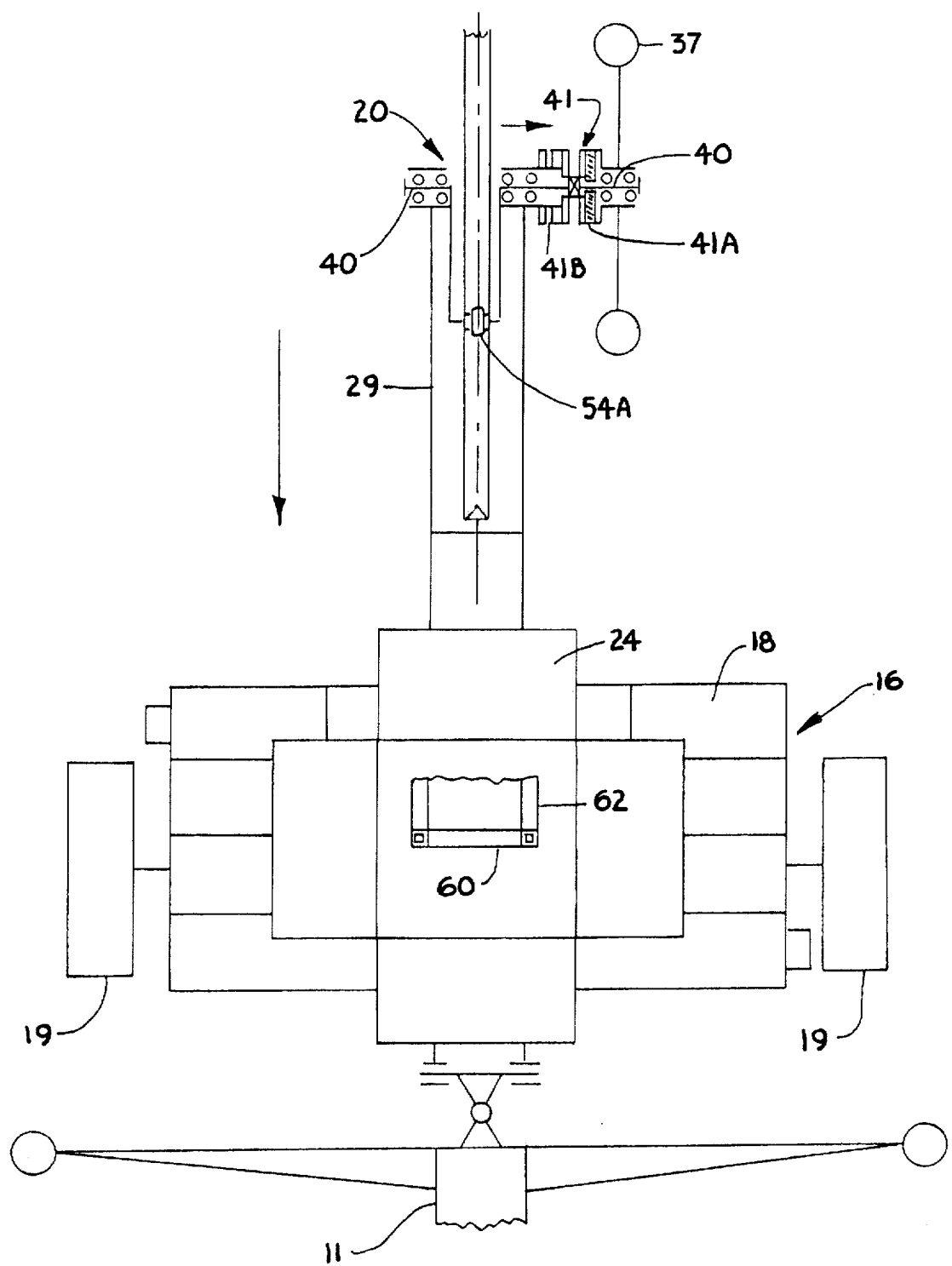
FIG. 2 is a fragmentary schematic top view of an automatic soil sampler.

The soil sampler 10 is a machine designed for automatic on-line soil sampling from the cultivated field. The soil sampler is attached to the vehicle 11 (FIG. 2), which has a boom 14 dropping the foam markers 13, the vehicle has a hydraulic system and electric power supply system.

Figure 3:
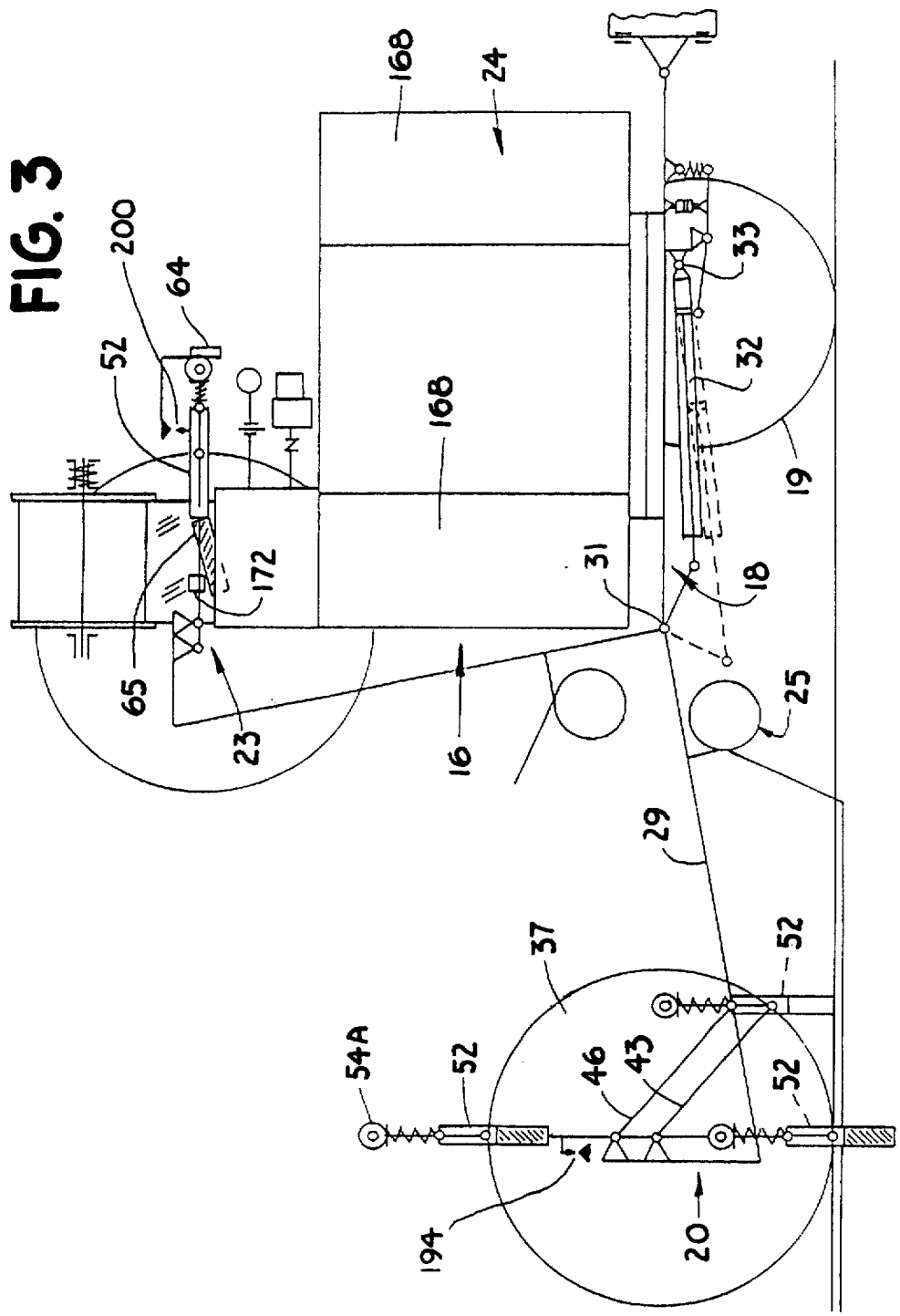
FIG. 3 is a schematic side view of the sampler of FIG. 2.

The automatic soil sampler consists of two-wheel attachable trailer 16 having a frame which is mounted on wheels 19 (FIG. 3). Soil sampling probe assembly 20, a sample packaging station 23, a packed sample container or collector 24, and a marker system 25 for marking the path of the soil sampler.

The soil sample 65 that is removed from the soil is lifted over the container 24 on the trailer 16, and is deposited between two sheets of plastic, heat sealed into an individual package, and then the individual sample is stored until it is taken to a testing station.

The soil sampler 10 as stated is a trailing unit with a trailer 16 having a frame 18. At the rear of the frame 18 is the sampling probe assembly 20, which is mounted on a pivoting frame 29 to the frame 18. The frame 29 can be made with a pair of legs 29A and 29B (see FIGS. 5 and 6), that are pivoted as at 31 at the rear of the frame 18. A hydraulic actuator 32 is attached at one end to the frame 18 as shown at 33, and the rod end of the actuator is attached as at 34 to the frame 29. The frame 29 has suitable braces, and pivots as a unit about pivot axis 31 when the hydraulic actuator 32 is extended or retracted. The outer end of the frame 29 mounts a sampling probe assembly 20, including a wheel 37 that engages the ground, and is rotatably mounted with a suitable hub 38 supported on the frame member 29A, in a suitable manner to a shaft 40. The wheel 37 is permitted to rotate on shaft 40 which is supported in a hub 38 fixed to frame 29 with a support block 38A. A clutch and brake assembly of conventional design and indicated schematically at 41 is used to apply a brake to shaft 40 and disengage wheel 37 to permit it to freely rotate and to engage a clutch to drivably connect wheel 37 to shaft 40 and permit shaft 40 to rotate in another position. The two positions of the clutch, and brake 41 are controlled electrically and can be preprogrammed. A single revolution clutch, that is a clutch that permits one revolution of the wheel each time it receives a signal and otherwise locks shaft 40 while wheel 37 rotates, also can be used. The brake can be a positive stop gear and dog arrangement.

Figure 6:
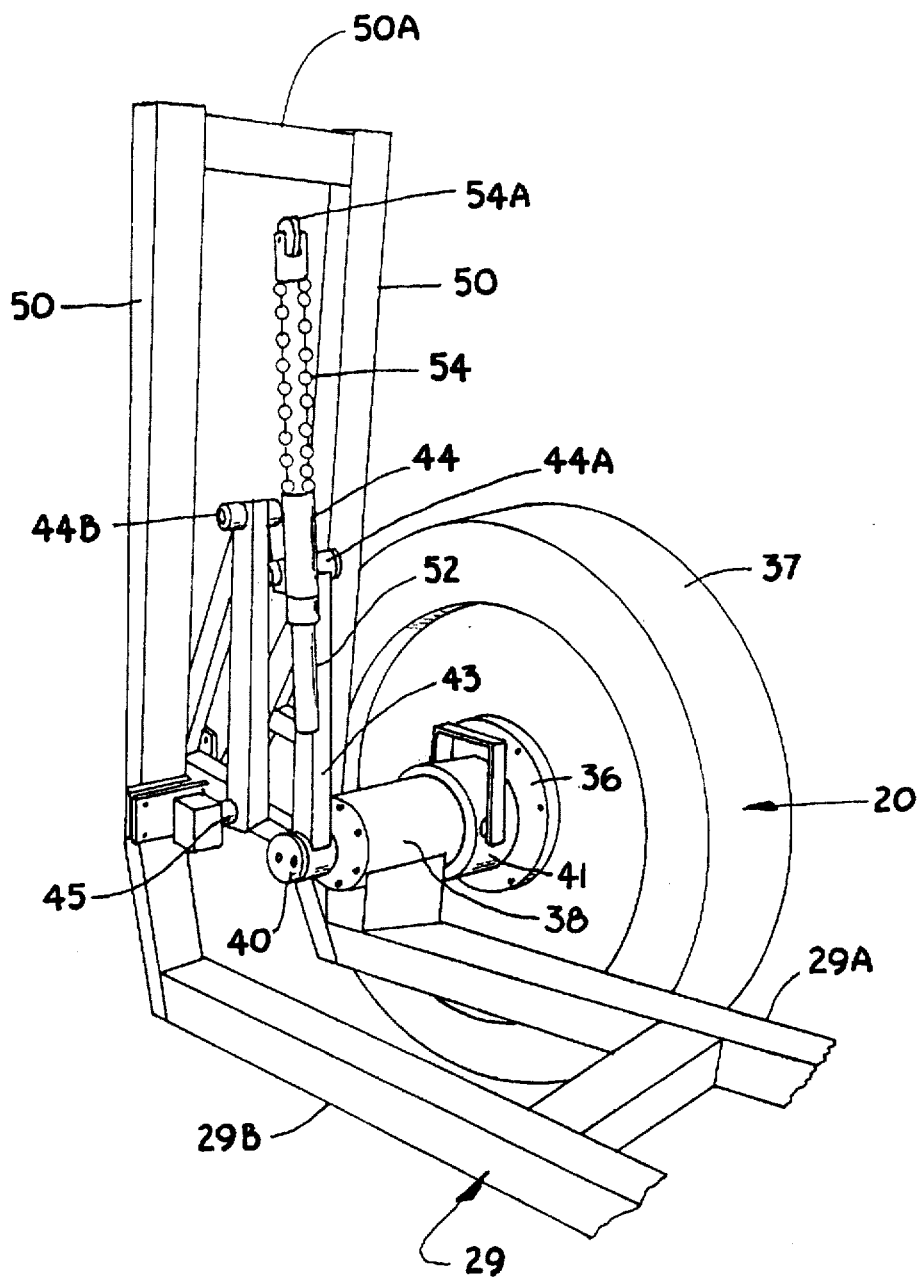
FIG. 6 is a perspective view of the soil sampling probe and drive wheel assembly used with the device of FIG. 5.

When the clutch engages the wheel 37 will drive the shaft 40. The shaft 40 in turn is drivably connected to a drive arm assembly 43, and as can be seen in FIGS. 5, 5A, and 6. An outer end of drive arm 43 pivotally mounted at 44 to a soil sampler probe mounting block 44. The probe mounting block 44 movement is controlled by arm 43 and a parallel linkage arrangement including a control link 46 having an end pivotally mounted at 44B to the probe mounting block 44, and also pivotally mounted at 48 to a support block 48 attached to an upright frame assembly 50. Frame assembly 50 attaches to the frame 29. The probe mounting block 44 rigidly mounts a tubular soil probe 52, which is of conventional design having an end portion 52A which will penetrate the soil. A cylindrical sample or core of soil will be received in the interior of the probe 52, when the probe penetrates the ground as shown in dotted lines in FIG. 5. An ejector rod 54 is slidably mounted in a bore in the probe mounting block 44, and will slide through the interior of probe 52, when pushed in the direction to eject the soil sample from the end 52A of the probe. A roller 54A is used at the outer end of the rod 54, and a spring 54B holds the rod 54 in its retracted position, as shown in FIG. 5, under normal conditions.

The parallel links comprising the drive arm 43 and the control link 46 will maintain the probe 52 in a substantially vertical position as it is rotated by drive arm 43 and the drive wheel 37 when the clutch 41 is engaged.

The start and end of each cycle is shown in dotted line position in FIGS. 5 and 5A. As can be seen in FIG. 6, the frame 50 has two upright legs, with a cross bar 50A at the top, but in the position shown in FIG. 5A, the probe 52 will be nearly at a maximum height position with the roller 54A spaced away from frame 50 slightly relative to when the clutch 41 disengages and locks shaft 40.

While the wheel 37 for the driving and sampling probe is shown as a smooth wheel, it can have suitable drive lugs or thread and preferably is a pneumatic tire.

Frame 29 and the upright frame 50 will move as a unit when pivoted by actuator 32, and carry the wheel 37 and probe assembly upwardly when the actuator 32 is extended. This will move the wheel 37 to the dotted line position shown in FIG. 5. As the frame 29 moves upwardly, it can be seen that the frame 50 and the roller 54A of the rod 54 will move to overlie a packaging unit support frame 60 that is supported on the trailer frame 18, and extends upwardly. There is an upright frame member 61, as shown at the rear of the trailer frame, and a horizontal overhead frame member 62 all of which are positioned so that they do not interfere with the trailer body or container 24 on the trailer frame 18.

The frame 60 includes an actuator plate shown at 64, at the front of the frame, and as the pivoting frame 29 is moved up over the top member 62, the roller 54A will engage the plate 64, and this will cause the rod 54 to be pushed into the probe 52 and expel any soil sample that is contained therein. Such a soil sample is shown at 65 in FIG. 5. The rod 54 can have an end plate that fits closely on the interior of probe 52 to aid in pushing the soil sample out.

Actuator plate 64 is made so that it will fit in between the upright members of frame 50. The cross member 50A is moving in an arc, as frame 29 pivots and the plate 64 is made to be clear of the cross member 50A as the cross member moves past the plate 64.

When the frame 29 is in its dotted line position shown in FIG. 5, the soil sample 65 will be ejected into a region between a pair of sheets of plastic shown generally at 68 in FIG. 5 that will be used for packaging the soil sample in packaging assembly 23 that is supported on a frame 70 of suitable design. Frame 70 in turn is supported on the frame 62. Schematically this arrangement is shown in FIG. 3 as well, with the soil sample 65 being pushed out of the probe 52.

Figure 11:
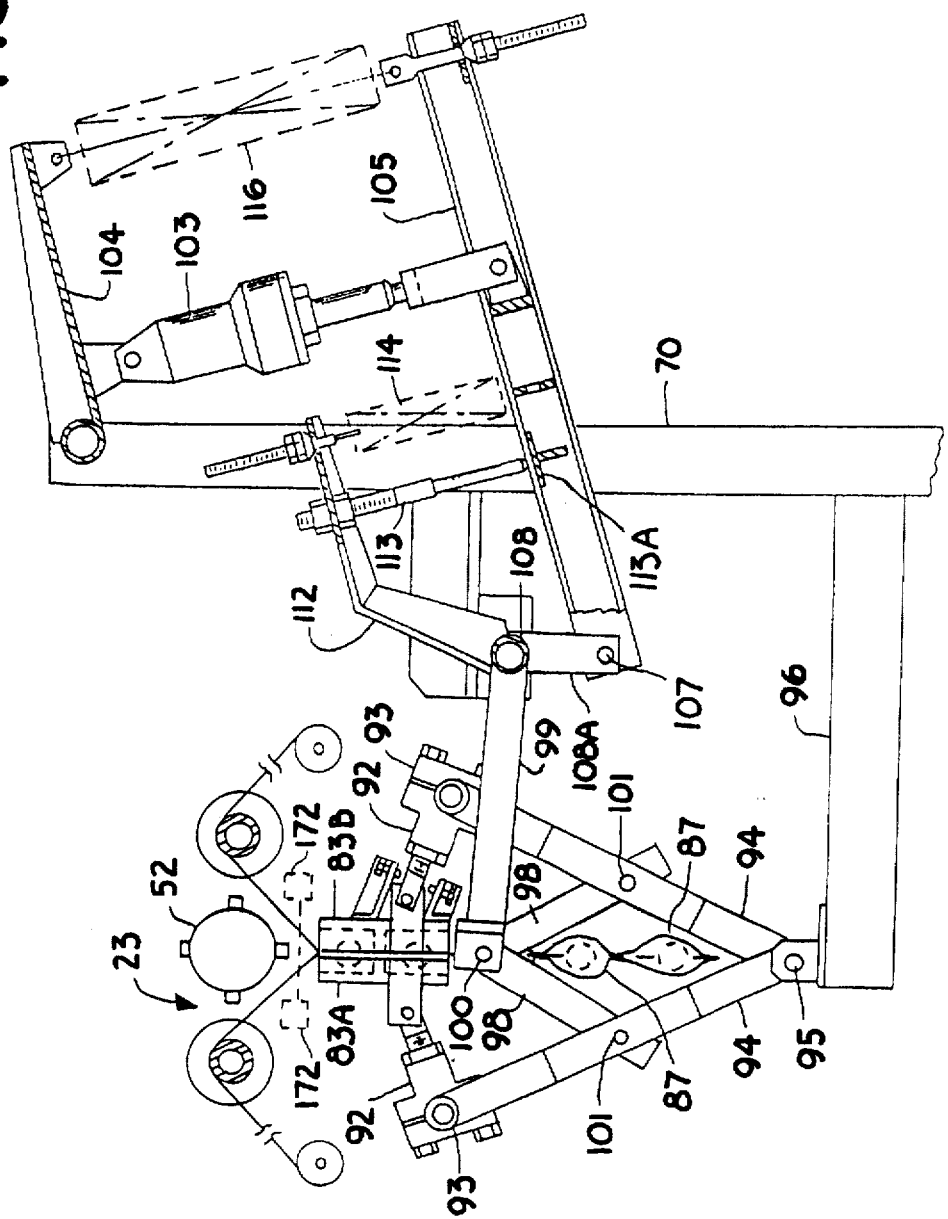
FIG. 11 is a side view of the heat sealer control linkage arrangement shown schematically and alone for purposes of illustration.
Figure 12:
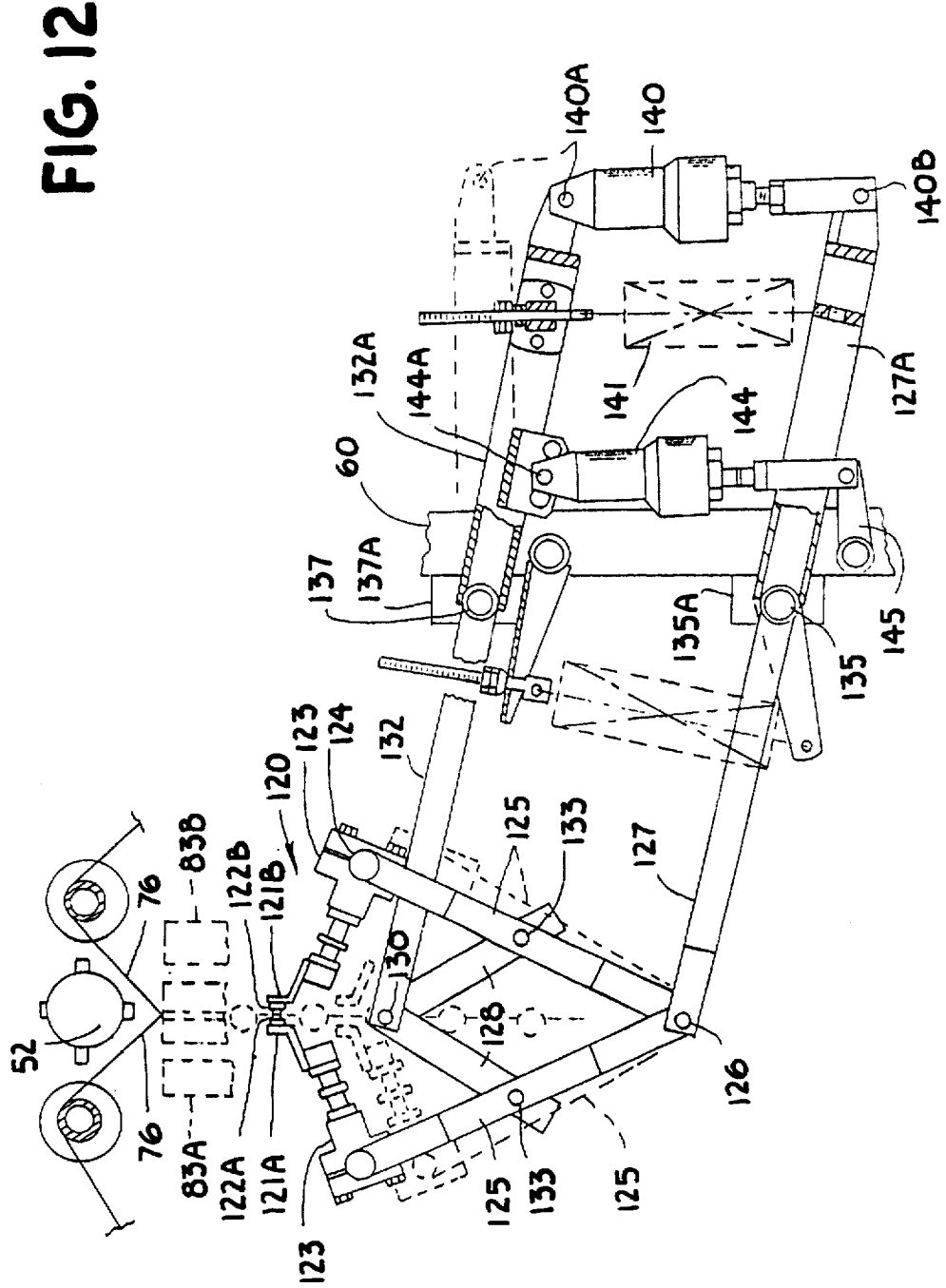
FIG. 12 is a side view of a package material moving or advancing linkage arrangement shown individually and schematically for purposes of illustration.

In FIGS. 11 and 12, the end view of the probe 52 in the position in which it is placed when the soil sample 65 is being dropped. It should be noted that the probe 52 is not aligned with the supply rolls of plastic in which the soil samples will be packaged, so the soil samples, when ejected will fall between the sheets coming from the rolls.

Figure 4:
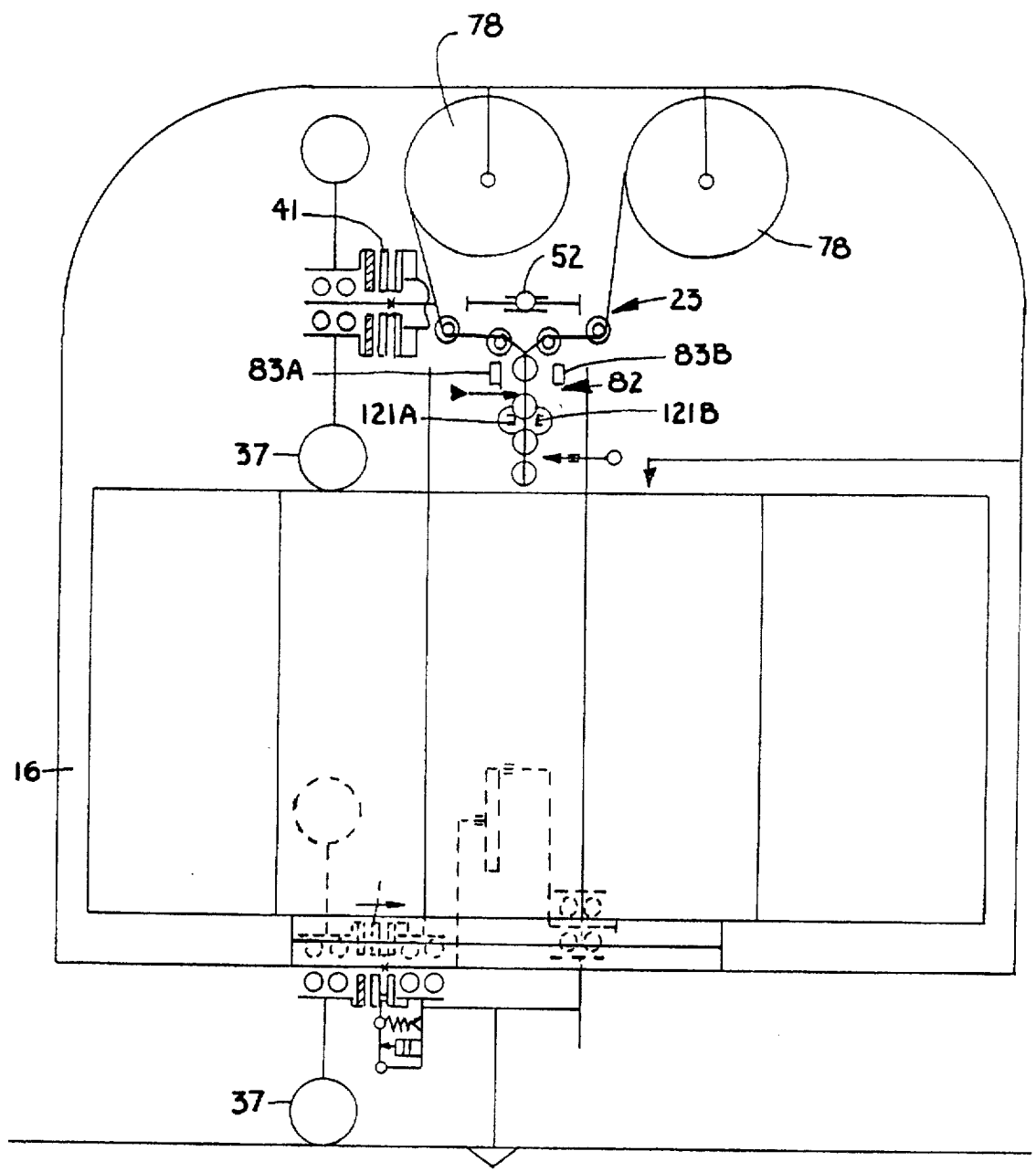
FIG. 4 shows a schematic rear view of the sampler of FIG. 2.

In FIGS. 9, 9A, 11, and 12, details of the packaging station 23 are shown. Sealed bags for the individual soil samples are formed in a long "chain" of samples. The schematic showing of FIGS. 3 and 4 is also referred to.

Frames 60, 62 and 70 are made to support the linkages. The packaging assembly 23 is mounted above a rear section or compartment of the trailer 16. The frame 60 is supported in an open center formed by four sample containers 165, as shown on trailer frame 18, and extends upwardly to above the trailer frame where overhead frame 62 and uprights 61 support frame 70 of the packaging station 23.

Figure 9:
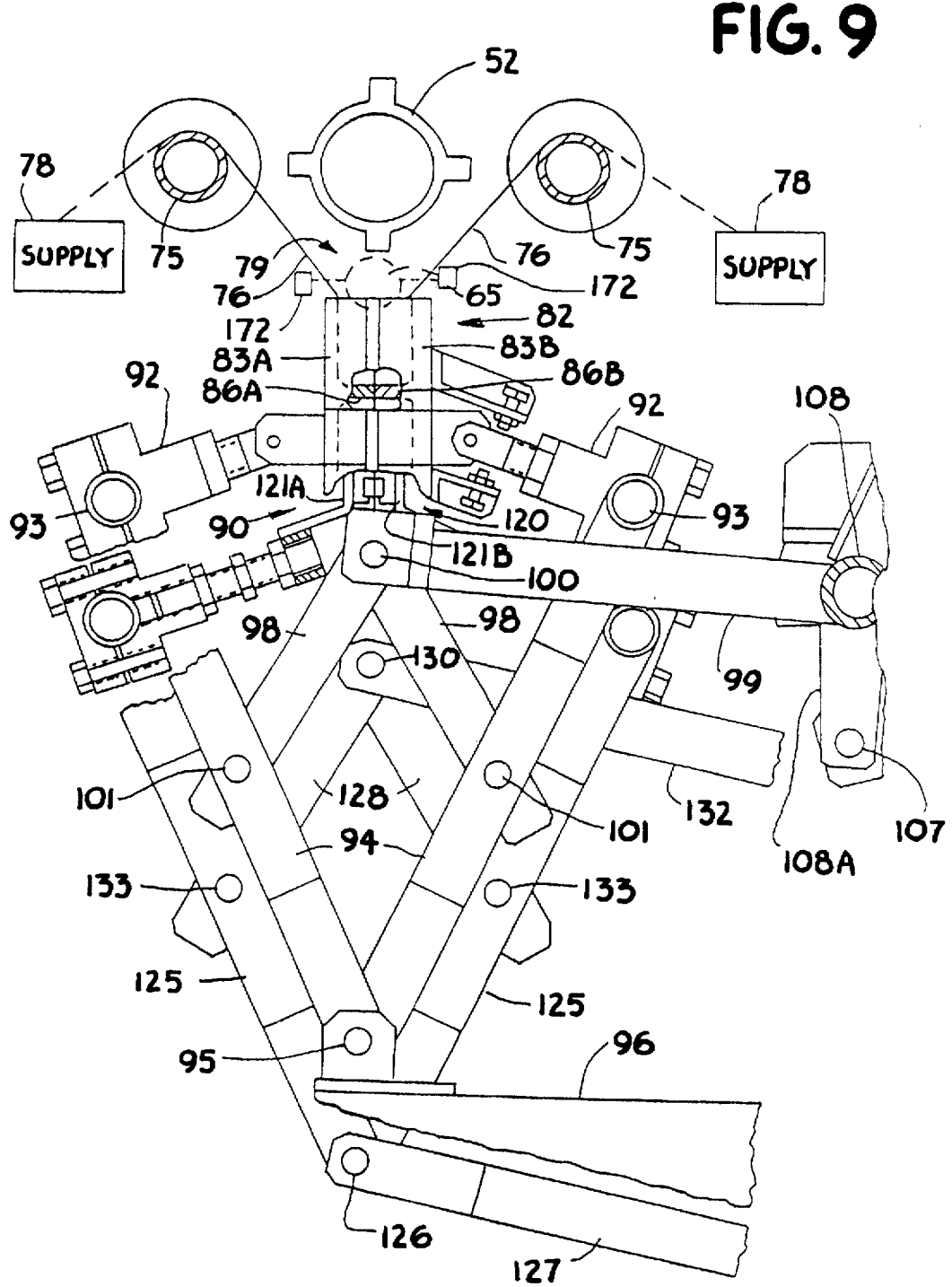
FIG. 9 is a fragmentary top plan view of a packaging station utilized with the soil sampler.
Figure 10:
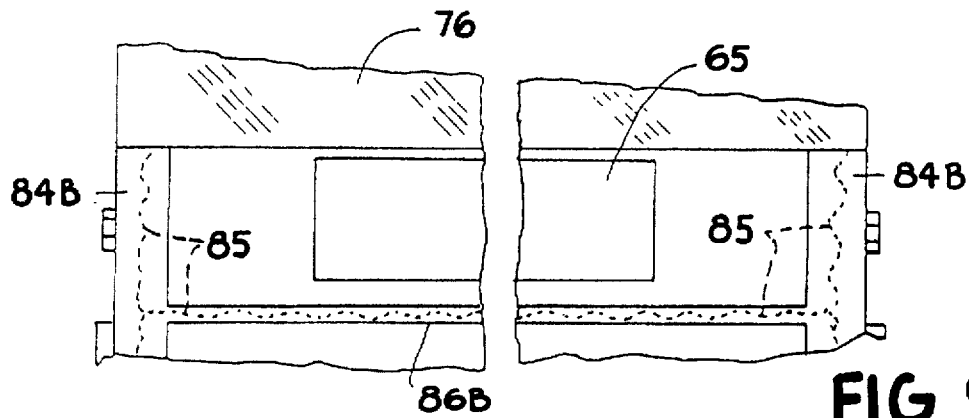
FIG. 10 is a view of a heat sealer section bar for the packaging system.
Figure 9A:
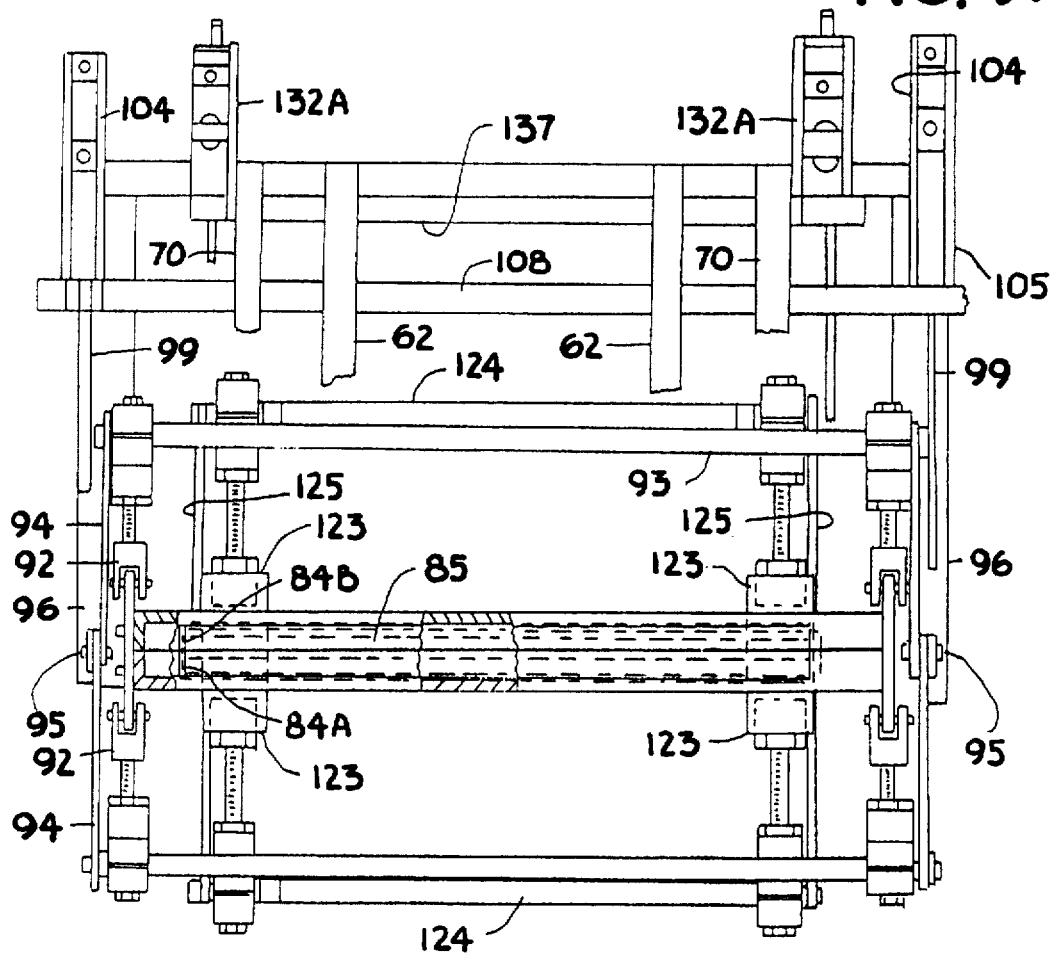
FIG. 9A is a side view of the packaging station used with the soil sampler.

FIG. 9 illustrates an end view of the linkage used. The probe 52 is positioned between a pair of guide rolls 75, 75 that are rotatably mounted on opposite sides of the probe 52. The rolls 75 guide sheets of suitable plastic film indicated at 76 from suitable supplies 78. The supplies are large rolls that are rotatably mounted in a convenient location. The guide rolls 75 position the sheets 76 so that they are spaced apart sufficiently to permit the probe 52 to pass between, and so that when the probe 52 expels the soil sample 65, the samples will drop into the "bight" portion indicated at 79. The bight portion 79 is immediately above a heat sealing station indicated at 82 which has a pair of operable and closable heat sealers 83A and 83B. The heat sealers 83A and 83B are generally "H" shaped, with a long center bar 86A and 86B (parallel to the axis of the probe 52). The heat sealers 83A, 83B have end edge portions 84A and 84B that mate along a parting line and sealer 83A has a resilient gasket on its edges for compressing the plastic together. When the heat sealer 83A is heated with a suitable electric heater 85 (FIG. 10), and as the heat sealers 83a, 83B are moved together, they seal the two sheets of plastic from supplies 78 together to form a package. The edge portions 84A, 84B and bars 86A, 86B will mate to seal the parts of the two sheets 76 aligned with the mating surface. When the heat sealers are closed and positioned as shown in FIG. 9, the plastic sheets 76 will be spaced apart at bight portion 79 above the heat sealer sections, but will be fused together along the edges 84A and 84B, as well as along the center rib 86, to form a pocket that is open at the top. This sealing will also close off any previously formed pocket that is in the lower parts of the heat sealers 83A and 83B and below, and will seal along the edges or ends as well as along the top of the lower section to form a soil sample package 87 (FIG. 11).

The sealers 83A, 83B are controlled to reciprocate, and move away from the plastic sheets a sufficient amount so that a soil sample core indicated in dotted lines at 65 in FIG. 9 will be permitted to pass between the bars 86A and 86B to permit the sealed plastic sheets to be pulled down for receiving the next soil sample. When the sealers 83A and 83B are opened or retracted, a soil sample package advancing mechanism shown at 90 will be actuated to pull the plastic sheets and the package that has been previously partially formed and the soil sample for that package 87 downwardly sufficient to advance the plastic sheets one step. The soil sample that previously was above the bars 86A, 86B now would be below the bars 86A, 86B. The sealers 83A, 83B are then closed again to seal the top half of the previously formed package and enclose that soil sample, and form the bottom half of a new package 87. The bottom half of the new package is separated from the previous soil sample by the seal along bars 86A, 86B. The package advancing mechanism and the operation of the heat sealing members are synchronized to achieve this result. The packages 87 are left in a strip.

The individual linkages for the heat sealing station 88 and advancing mechanism 90 are shown separately in FIGS. 11 and 12, and are shown together in a front view relative to the overall soil sampler in FIG. 9. A schematic top view is shown in 9A. These figures illustrate one way that linkages can be mounted, but other ways can also be utilized.

The two heat sealer sections 83A and 83B extend across the packaging station and are mounted on opposite ends of each of the heat sealer members. The links 92 are connected to cross pipes shown at 93 so that they form a "yoke" that extends to opposite ends of the heat sealers 83A and 83B. A pair of arms 94, respectively are connected to opposite ends of the tubes 93, on each end of heat sealers and the pair of arms 94 on each end are mounted to a common pivot pin shown at 95. The pin 95 is supported on a bracket connected to a fixed arm 96 that is supported back to a frame member of frame 70. A scissor type linkage 98 is connected between the arms 94 on each end of the heat sealers 83A, 83B, and is operated through a control arm 99 that pivoted as at 100 to first ends of both of scissor links 98 on each side of the heat sealers. The pivot 100 is a common pivot for the pair of scissor links 98. The opposite ends of the scissor links 98 are connected at pivots 101 to the respective arms 94.

The arms 99 are fixed to a cross tube 108 that is pivoted on supports forming part of frame 70. The cross tube 108 and arms 99 are operated by a hydraulic actuator 103 that in turn is mounted to a fixed arm 104 (FIG. 11) attached to the frame 70 in a suitable manner, and in a proper position by utilizing a fixed tube 104A to properly position the arm 104. The actuator 103 in turn has its rod end connected to an arm 105 which is part of a pivoting assembly including the arm 99. The arm 105 is pivoted at 107 to a control arm 108A that is attached to cross tube 108 to which arms 99 are attached.

The tube 108 has a stop and control arm 112 attached thereto as well. A stop member 113 is mounted on this control arm and overlies a cross piece 113A on the arm assembly 105, and provides an abutting stop as arm 105 pivots upward about pivot 107. A spring 114 is attached to the control arm 112 as well, and provides a force urging the arm assembly 105 toward the stop 113.

As the actuator retracts, the arm 105 will be lifted against a stop member 113 and arm 99 will move the pivot 100 downwardly and separate the upper ends of the links 94, and thus move the arms 92 apart, thereby separating the heat sealers 83A and 83B.

The stop 113 is adjustable and when the actuator 103 is retracted, the amount that the arms 99 move can be adjusted. The force from the actuator 103 will cause pivoting of the tube 108 relative to its support back to the frame 70, and cause the scissor linkage to open up the heat seals 83A, 83B. The spring 114 will be extended when the actuator 103 extends and urges the arms 99 upwardly as arm 105 moves downwardly. The closing of the heat sealers by action of the scissor links as pivot 100 moves upwardly is under spring force of spring 114 when the actuator 103 is fully extended and the heat sealers are in engagement. plate 113A is spaced from the end of stop 103 so the heat sealers 83A, 83B are spring loaded together.

FIG. 12 provides a more detailed view of the linkage utilized for the sample package advancing mechanism 90, mechanism 90 pulls the packages containing the soil sample downwardly to pull lengths of plastic sheets from the supply rolls 78 after the heat sealing members 83A and 83B have been retracted or opened so that they are not engaging the plastic sheets 76.

The frame 70 is used for mounting a linkage assembly 120, which includes a pair of sheet clamps indicated at 121A and 121B that have resilient pads 122A and 122B on each side of the plastic sheets, and these pads are positioned so that they will engage the sheets approximately at a location where the previous cross sheet heat seal was made by the bars 86A and 86B. The pads are essentially parts of the clamp assembly including a separate pair of brackets 123, on each outer side of the two plastic sheets 76. The pair of support brackets 123 on each side of the plastic sheet are mounted onto cross tubes 124, which extend across the width of the plastic sheets. Support links 125 are attached to opposite ends of each tube 124. The support links 125 on each end of the mechanism have outer ends pivotally mounted at a common pivot 126.

A pair of scissor links 128 on each end of the package advance mechanism pivotally mounted as at 130 at their first ends (on a common pivot) to a second arm 132. The arms 127 and 132 form a parallel linkage, as will be explained. The opposite ends of the scissor links 128 are pivotally mounted as at 133 to mid portions of the control arms 125, 125 on each end of the package advance mechanism.

The arms 127 are mounted on a cross tube 135, and the cross tube has arm assembly 127A extending in opposite directions from arms 127.

The arm 132 is mounted onto a cross tube 137, that extends across the width of the package advance mechanism so that the arms 132 on opposite sides of the mechanism are joined together to move in unison. Arm portions 132A are fixed to tube 137 and extending in an opposite direction from the arm 132. Arm portions 132A are used as actuation portions.

The ends of the arm portions 132A and 127A have a hydraulic actuator 140 mounted between them. The actuators 140 are mounted as at 140A to the end of the arm 132A, and as at 140B to the end of the arm 127A. The tubes 135 and 137 are pivotally mounted in suitable supports 137A and 135A to the frame 70, and supported in a suitable manner in the proper lateral location. When the actuator 140 is extended, pivots 130 and 126 will tend to move together causing the scissor links 128 to spread the arms 125 apart, so that the clamp members 121A and 121B will separate. A tension spring 141 can be provided between the arms adjacent the actuator 140 to provide a spring load to cause the actuator 140 to retract under the spring load and to spring load the clamp members 121A and 121B together.

The clamps 121A and 122A can be moved down to their dotted line position pulling the plastic sheets with them, along with any soil sample illustrated in dotted lines after the heat sealers 83A, 83B have opened by operating an actuator 144 that is mounted onto a fixed arm 145 that is attached to the frame 70, and which has its opposite end connected to the arm portion 132A. When the actuator 144 is extended, the mounting pivot 144A where the actuator mounts to the arm portion 132A will be moved upwardly as shown in FIG. 12 and this will cause the parallel links 127 and 132 to pivot on the tubes 135 and 137 and in turn move the pivots 130 and 126 downwardly in unison because of the parallel linkage arrangement. The actuator 140 acts as a link at one end of the parallel linkage.

Once the actuator 144 has moved the partially formed pocket at the top half of the heat sealers and the finished package below the heat sealers downwardly by a selected index amount, the clamp members 121A and 121B will be opened or retracted by extending the actuator 140, which moves pivots 126 and 130 together and spreads arms 125 as shown by dotted lines in FIG. 12. The cylinder 144 will then be returned to its solid line position shown at FIG. 12 with clamp members 121A, 121B aligned with a heat seal line for a sealed package containing a soil sample. The clamping takes place above a soil sample that has been fully packaged.

In the position shown in FIG. 12, the soil sample 65 indicated in dotted lines just below the dotted line showing of the heat sealers 83A and 83B will be held in a package that has been sealed on ends, with a cross sheet heat seal underneath the soil sample. The heat sealers 83A and 83B are again actuated and a soil sample just below the heat sealers is fully encapsulated in a plastic package with the complete heat seal at the top.

All of the soil samples shown in dotted lines will be in packages that will be left in a continuous chain. Each of the packages will be identified in a suitable manner, either by way of manual identification, or by knowing the start and end position of each pass or path and the distance from the start of a pass to correspond to the known position of the sampling probe when the particular soil sample was removed from the soil.

Figure 7:
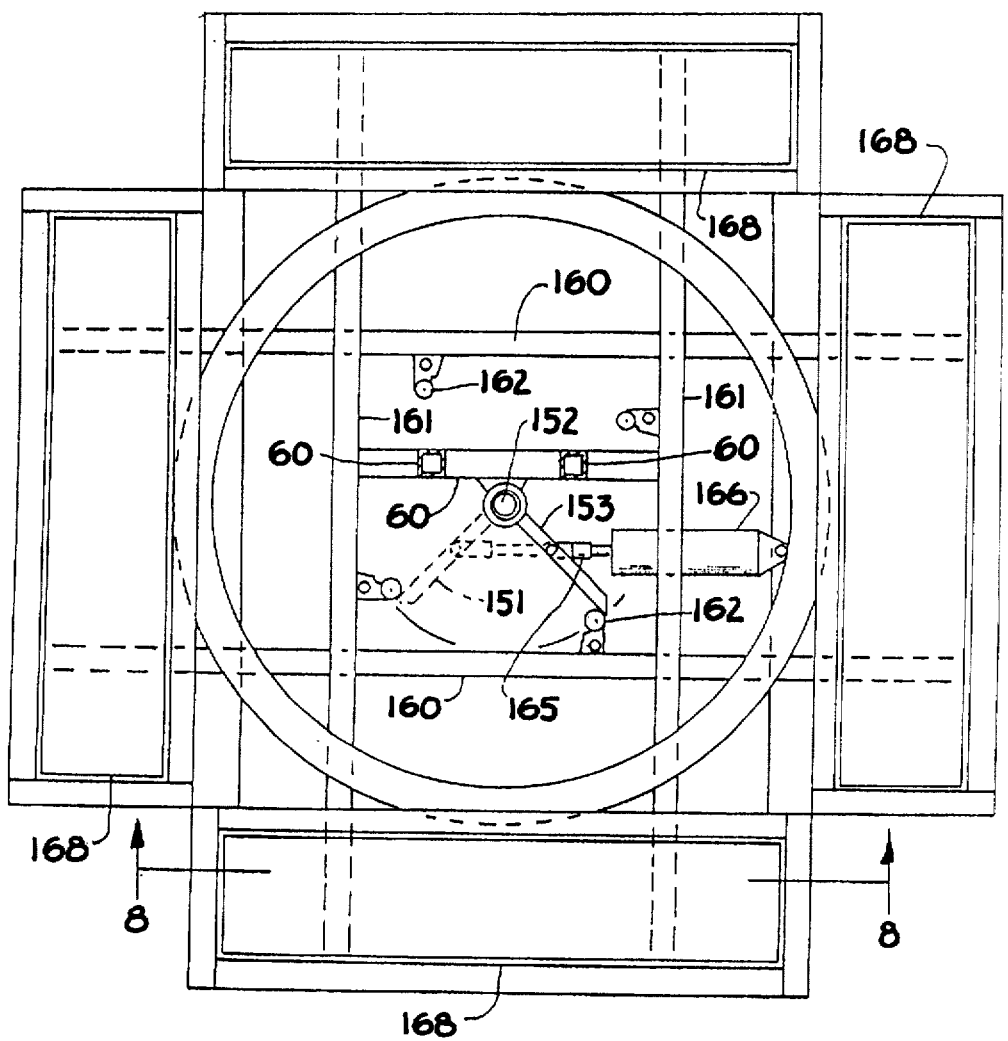
FIG. 7 is a top schematic view of an indexing device for indexing a sample storage trailer about an upright axis.
Figure 8:
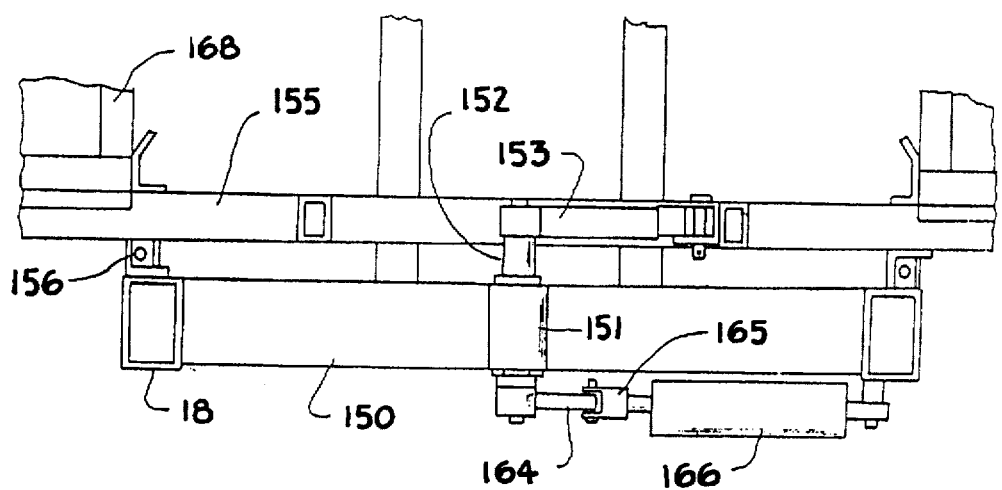
FIG. 8 is a view taken as on line 8—8 of FIG. 7.

In FIGS. 7 and 8, a schematic showing of a turn table type trailer assembly is illustrated. In FIG. 8, the main frame 18 is shown with a cross member 150 that mounts a hub 151 in which a turn table actuator shaft 152 is rotatably mounted. Actuator shaft 152 has an arm 153 attached thereto, which as shown, has the one beveled end, and is used for indexing a trailer rotating frame 155. The rotating frame is suitably mounted on a wall bearing arrangement indicated at 156 onto the frame 18, and the frame 18 can have suitable supports underneath the turn table frame 155 as desired. The turn table frame 155 has a number of cross members including inner cross members 160 and 161 on which drive rollers 162 are suitably placed. The drive rollers 162 as shown are at four different locations, and they are aligned vertically with the drive arm 153. The opposite end of the shaft 152 has a link 164 that is connected to the rod end 165 of a hydraulic actuator 166 which in turn is connected to the frame 18. When the actuator 166 extends to its dotted line position as shown in FIG. 7 it will drive one of the rollers 162 and will rotate the turn table 90°, as shown by the dotted line position of the arm 153. In this manner, four different sample hoppers or containers 168 removably mounted onto the turn table frame 155 can be positioned underneath the packaging assembly. The sealed packages of soil samples are deposited in the containers. These containers or hoppers 168 can be removed from the frame utilizing a suitable forklift, or other means, and then they can be transported to an analysis laboratory for running a complete soil analysis on the individual soil samples.

Figure 13:
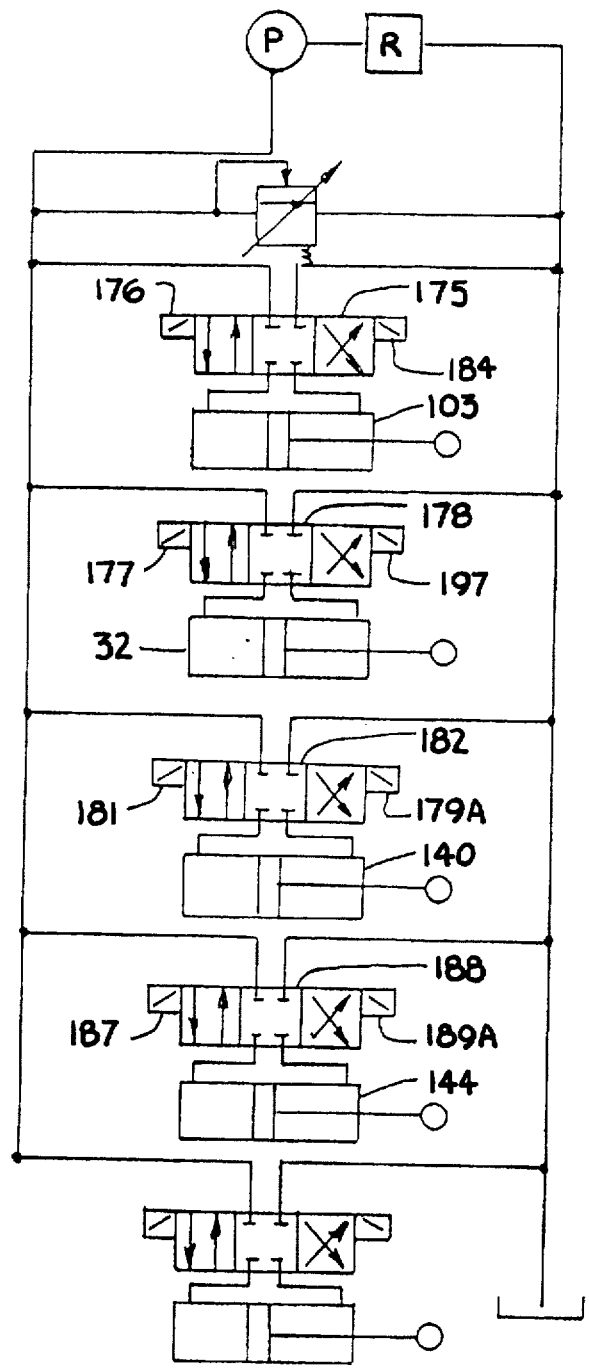
FIG. 13 is a schematic hydraulic diagram used with the automatic sampler.
Figure 14:
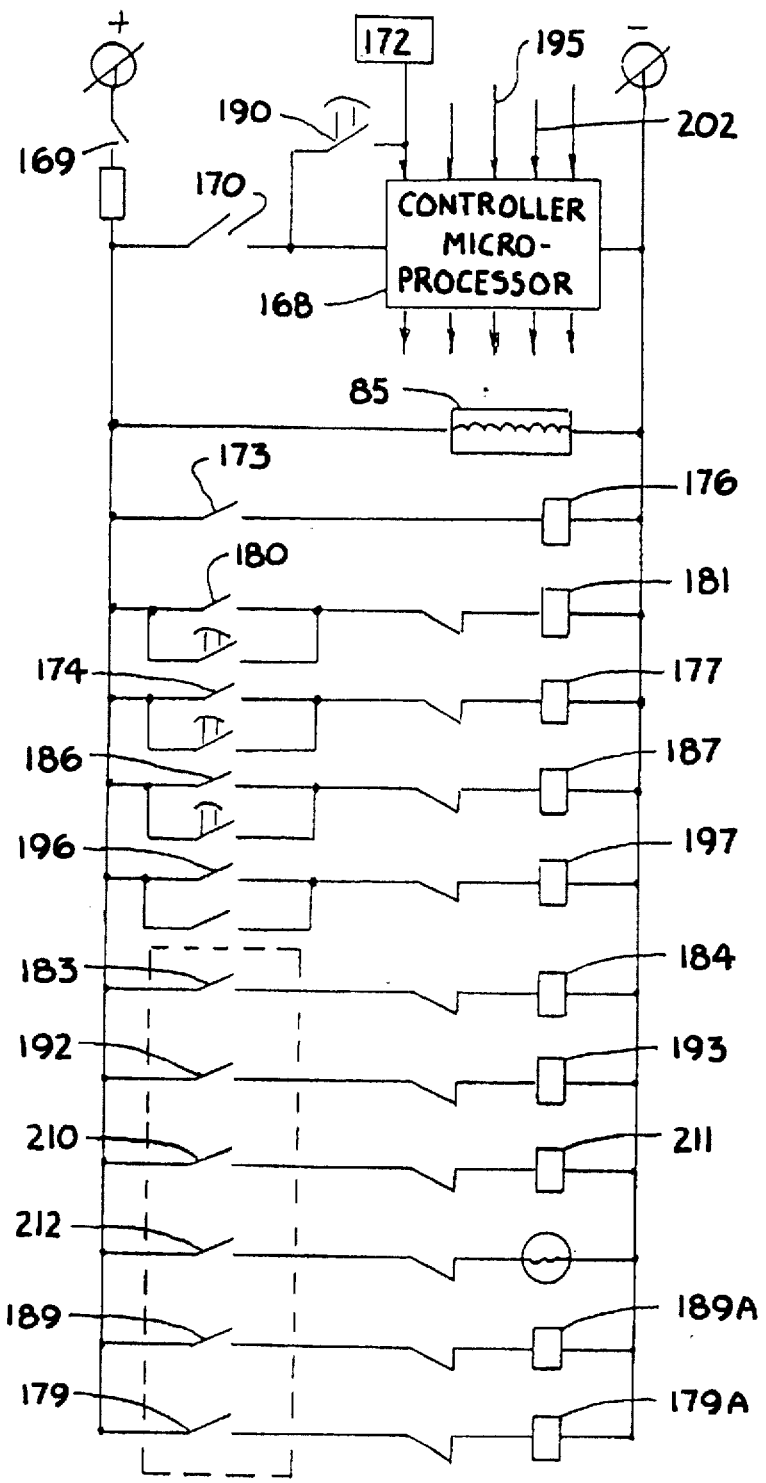
FIG. 14 is a circuit diagram of the controls for the automatic sampler.

The automatic soil sampler is placed at the beginning of the first pass in the field, and a controller 168 is turned on by a switch 169 of the control panel (FIG. 14). Heater 85 begins to operate when the switch is turned on. After the heater 85 reaches operating temperature, the controller turns on a switch 170 that operates either on a time delay or with a thermal sensor. A sensor 172 indicates that the probe is above the packaging station, and the controller 168 generates control commands to close switches 173 and 174 (FIG. 14). Switch 173 energizes a solenoid 176 so that the actuator 103 for the heat sealers is extended by operating a valve 175 (FIG. 13) and the arm 99 is moved up to close the heat sealers 83A, 83B. The plastic sheets are then sealed together with the heat sealers 83A and 83B, to form an open top package into which a soil sample can be dropped.

A switch 174 energizes a solenoid 177 to operate a valve 178 (FIG. 13), in turn operate actuator 32 and lower the frame 29 so that the wheel 37 engages the ground. After the delay necessary to seal the plastic sheets together to form the open top package, the control unit generates a signal to close the switch 180 to energize a solenoid 181 which actuates a valve 182 (FIG. 13) in a direction to operate the actuator 140 to retract and thereby clamp the plastic sheets between the clamps 121A and 121B.

Next, in the sequence, the controller 168 will open switch 173 and actuate a switch 183 to operate a solenoid 184 for valve 185 and cause the actuator 103 to retract, and pivot the arm 99 downwardly operating the scissor linkages to move the heat sealers 183A and 183B away from the plastic sheet, after of course, the heat seal has been completed.

When the heat sealers are opened the controller closes a switch 186. Then, the controller will actuate a switch 186 to energize a solenoid 187 to operate a valve 188 that will cause the actuator 144 to extend and move the arms 127 and 132 and the clamps 121A, 121B down, to in turn pull the sheet material that had been previously heat sealed in heat sealers 83A and 83B downwardly a desired indexed amount. The partially formed package is pulled through the open heat sealers.

At a desired time, after the plastic sheets have been advanced downwardly, the switch 183 will be opened, relaxing the solenoid 184 and switch 173 will close energizing the valve 175 to extend the actuator 103 and reclamp the heat sealers 83A and 83B in a new position on the plastic sheets to seal the top of the previously open top package and simultaneously form another open top package that is open at the upper ends of the heat sealers 83A and 83B.

The controller will open switch 180 and close a switch 179 that actuates a solenoid 179A to move valve 182 so the actuator 140 extends and the clamps 121A and 121B open. The controller will then at an appropriate time, actuate a switch 189 and open switch 186. Switch 189 energizes a solenoid 189A to cause valve 188 to move actuator 144 to raise the clamps to position them as shown in solid lines in FIG. 12, ready to repeat the advancing of the plastic sheets at the appropriate time.

At the start of each field pass as a way of identifying the soil samples taken during each run, a manual switch 190 is used to input a signal to the controller simulating a signal from sensor 172, to form three empty bags to indicate the start of a run or pass along the field. Then, a mere count of each succeeding package is needed for identifying the individual samples, and the location where each sample was taken so when applying fertilizer, for example, the proper amount is applied as determined by the analysis of each soil sample. Since the first pass is known the end and start of each subsequent pass also can be counted. The sequencing of the manual switch 190, can be delayed somewhat from one another so that the package sequence will be repeated. In the manual sequence, wheel 37 would continue to engage the ground and frame 29 would not be raised and lowered.

When the suitable indication of a start of a field pass or run has been made, as disclosed, by having three empty sealed packages formed in a row, the vehicle 11 will begin its motion along the path as shown in FIG. 1. Odometer sensor 11A will provide a signal of distance after the vehicle has moved a desired amount from its start. The controller will close a switch 192 to energize a solenoid 193 which will cause the clutch-brake 41 to be moved to engage the clutch shown at 41A in FIG. 3, to couple the wheel 37 to the shaft 40, and release the brake or lock (41B in FIG. 3) so that the shaft 40 can be rotated as the wheel 37 turns.

The arm 43 will drive the probe mounting hub 44, and the probe 52 so that the probe will enter the ground as shown schematically in FIG. 3, while the probe maintains its vertical orientation. The forces for inserting the probe into the soil is provided by holding the actuator 32 at its lowest position, and the pressure in actuator 32 can act against a suitable relief valve so that a suitable amount of soil for a sample is captured in the probe, and held inside the probe by the friction force. If the probe encounters a solid object such as a stone or the like, the wheel 37 will actually be raised up against the force of the cylinder 32 because of the yielding permitted by the relief valve and the probe will continue to penetrate the ground while the vehicle moves forwardly to rotate the shaft 40 until such time as the wheel 37 again contacts the ground and lifts the probe up from the soil.

When the probe 52 reaches its upper position in rotation with shaft 40, as sensor illustrated schematically in FIG. 3, provides a signal along a line 195 to the controller 168 indicating that a sample has been received in the probe. The controller opens switch 192 to disengage the clutch 41A and set the brake or lock 41B. Also, the controller opens switch 174 and closes a switch 196 to energize a solenoid 197 and operate the valve 182 in a direction to extend the actuator 32 and lift the frame 29 and the probe assembly upwardly to its position overlying the packaging station. The soil sample comprising the core of soil taken is ejected by movement of the rod 54 as the roller 54A acts against the plate 64. Schematically shown, sensor 172 (FIG. 3) indicates when the probe 52 has reached its ejection position, so that the soil sample 165 is removed from the probe 52, and there is a signal input along a line 202 to the controller (FIG. 14). This is the first sample in a vehicle path, and an appropriate mark was made on the open top package that had just been formed by the heat sealers 83A and 83B for identification of the sample that is dropped into the open top package.

The operational cycle is then repeated, and the probe is lowered by operating the actuator 32 in an opposite direction by opening the switch 196 and engaging switch 173 and solenoid 177 to operate the valve 182 in an opposite direction to cause the actuator 32 to retract and lower the frame 29. The wheel 37 and probe again will be held in place with a suitable relief valve as explained.

The process repeats with the sealers 83A and 83B opening, the clamps 121A and 121B being moved downwardly by operation of the linkage and actuators, and then the heat sealers being reclamped, and the clamping mechanism 121A and 121B being reclamped at a new position on the sheets. Many of the solenoid operated switches have manual bypasses, as illustrated, so that manual cycling can occur if desired. During the operation, if a sample is not packed into the bag or a sample is not available, due to encountering a solid object or some other cause, the sensor 20 that is used for indicating a sample present, along a line 201, is activated, and the control unit generates a command which closes a switch 212, to light a warning light 213. The power can then be turned off until appropriate adjustment is made manually and then restarted.

The sealed packages containing the soil samples, are again left attached to each other until one of the containers on the trailer is filled, and then the containers are cycled, after the plastic sheets are slit, so that a new container is below the packaging assembly. The sealed packages can be delivered to a testing station, for processing in sequence, with each analysis being keyed into a particular location on the field as determined by the location of the sampling probe for each sample and the information provided by the odometer signal. The microprocessor controller 165 can record the different location on each pass as desired and thus analysis in each grid location for individual soil samples can be tied directly back to that location for fertilizer application. Numeral location of samples on each pass also can be used with the respective passes being identified by leaving empty packages between the end of one pass and the start of another.

Figure 15:
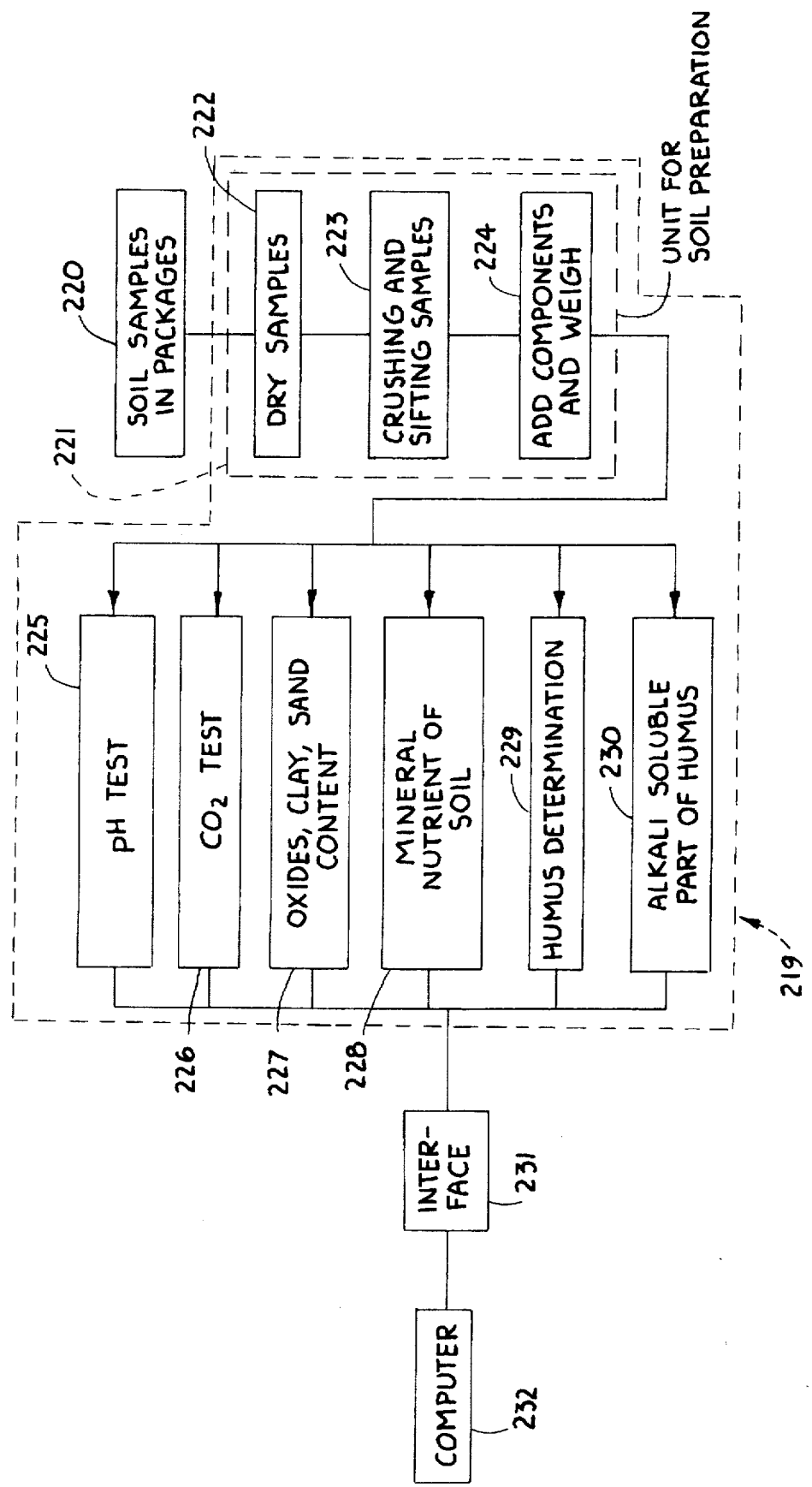
FIG. 15 is a block diagram of a soil sample analysis work station.

The workstation 219 for sample analysis includes several units as illustrated in FIG. 15, and the important feature is that the individual samples are maintained throughout the testing so that each sample from each grid is individually analyzed, and then the individual needs of fertilizer for that grid can be provided.

In FIG. 15, once the packages of individual samples are obtained, the container or string of packages indicated by the box 220 is put through a soil preparation unit 221, which is outlined in dotted lines. This includes the drying of the soil represented by box 222, the crushing and sifting represented by box 223, and the addition of liquid or other components that are necessary for normal soil sampling, and also the weighing of the sample represented by the box 224. The soil samples are then placed into a number of test procedures, which can be done sequentially, but each individual sample is tested in a pH line, represented by box 225, carbon dioxide represented by box 226; oxides, sand, and clay percentages are determined by box 227; a line for determining the mineral nutrients of the soil represented by box 228; humus determining line 229; and a line or station for determining the alkali soluble parts of the humus indicated by box 230. The tests can be run with portions of the sample, or it can be run in sequence, but each separate soil sample 65 is analyzed for these various components at a minimum, and additional tests can be conducted as desired.

An interface 231 is provided for the test result outputs, and then the tests are analyzed in a computer 232. The information can be stored in memory and transferred to disks for use with on board computers of a fertilizer applicator or other vehicle. The type of tests can be those that are known, or additional tests, as they are developed. The analysis will give a determination of the amount of fertilizer that is needed for that particular small grid as exemplified by each soil sample.

Figure 16:
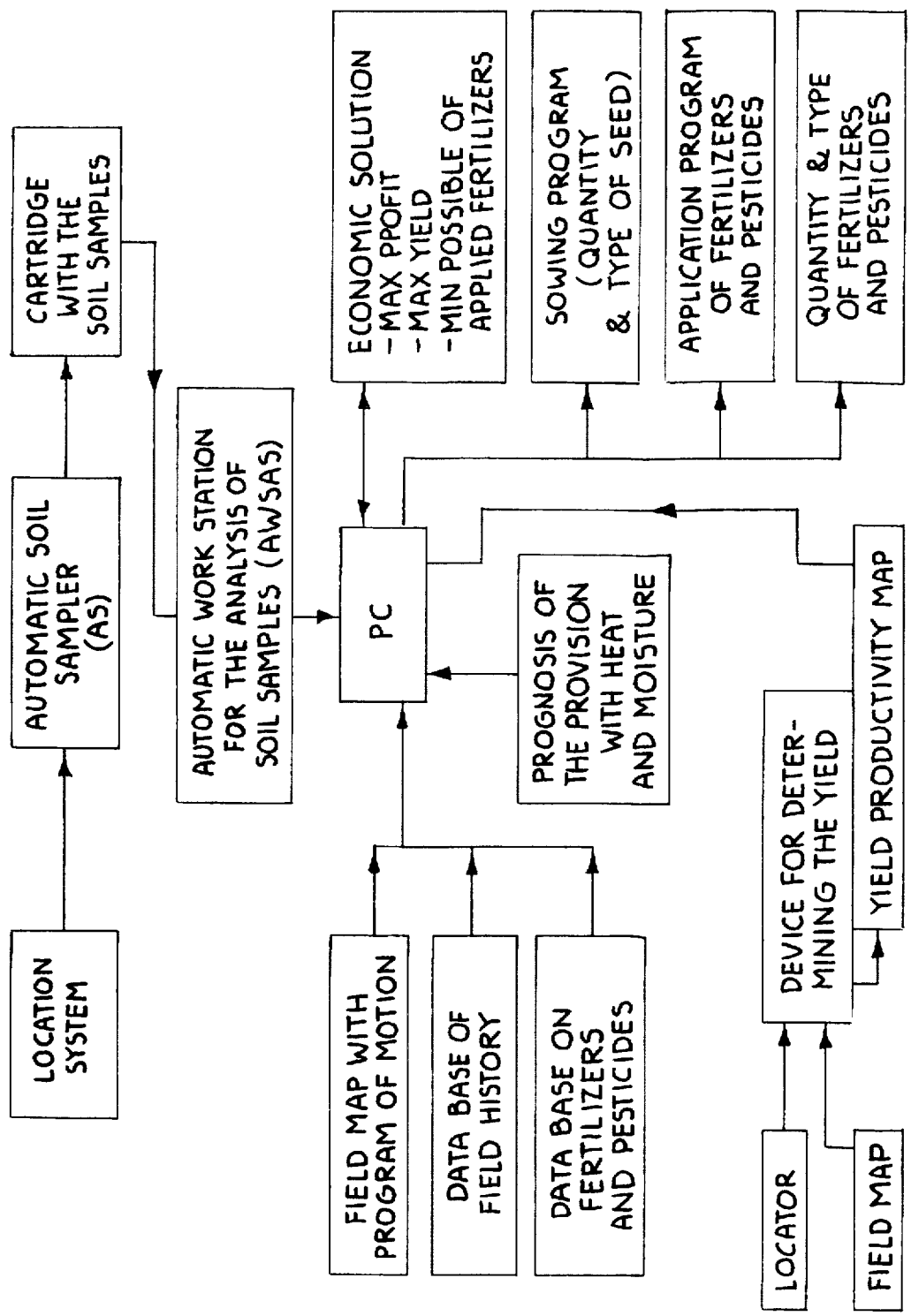
FIG. 16 is a block diagram for preparing a program of material application onto a field from which soil samples are taken.

FIG. 16 illustrates a functional diagram for types of information that can be determined utilizing the functions that were obtained by the soil analysis. The inputs to the personal computer are is shown. The inputs have been previously described including the location system for the location of the samples, the automatic soil sampler, the sealed package with the soil samples, and then the work stations that analyze the individual soil samples. Additional inputs to a computer program can be as those shown including a field map, a data base for fertilizer and pesticides, a data base of field history, and other inputs as desired. The computer memory stores in its data base or as an input, data on crops (kind of crop, seed variety and price, fertility requirements, estimated price of harvested crops). The computer stores data on fertilizers and well such as type, quantity of the active substance per mass unit, and application costs. Herbicide information such as type, unit price, application cost is stored. Also environmental factors such as heat effect and moisture expected provide input. Other economic factors can be programmed in. The outputs can be an economic solution such as maximum profit, maximum yield, and minimum possible of applied fertilizer according to developed programs. Also the application of fertilizers and pesticides based on the soil analysis can be determined, as can the quantity and type of fertilizers and pesticides needed. Based on the soil analysis a program for seeding or sowing seeds in each individual grid can be developed.

Figure 17:
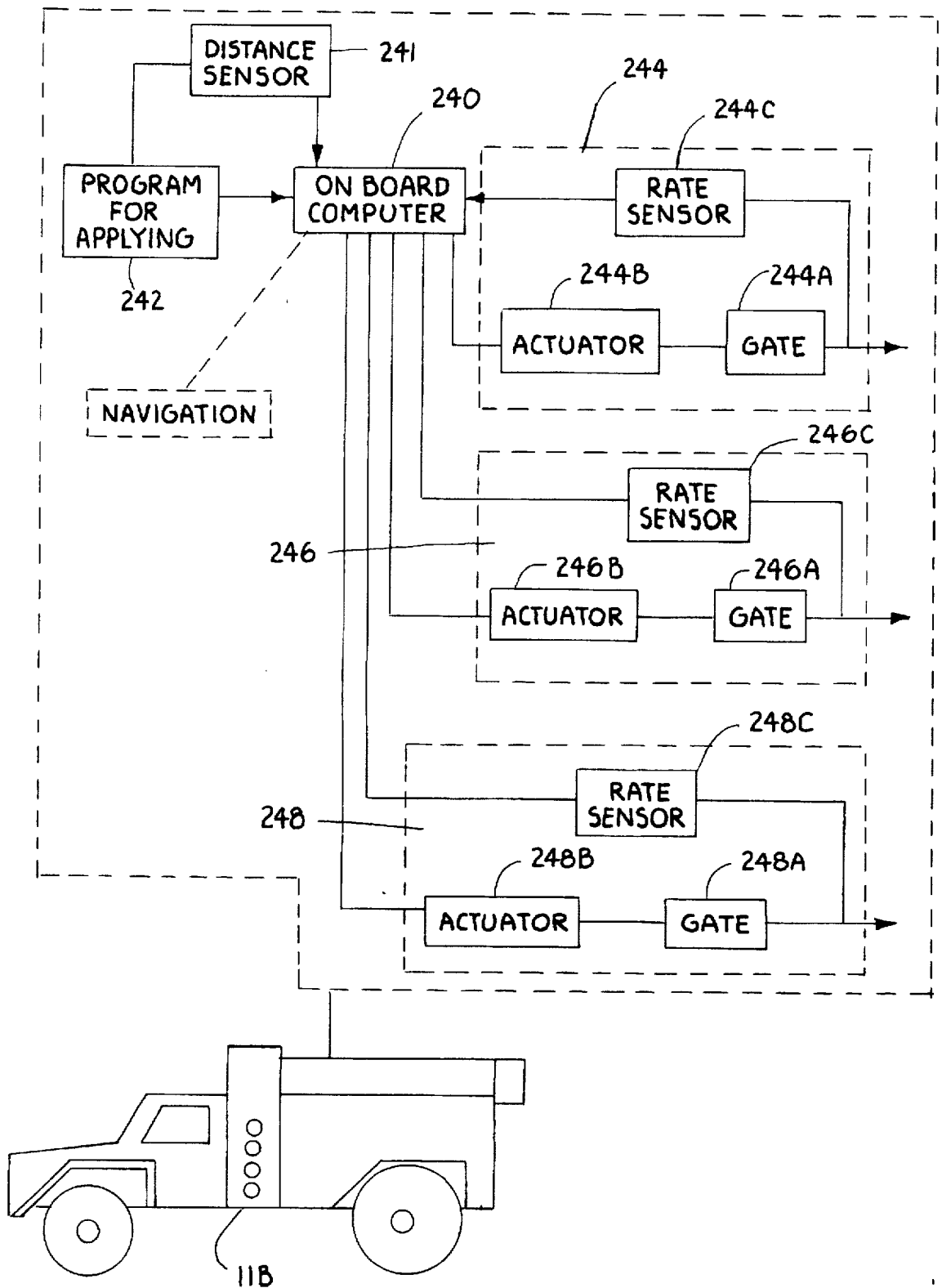
FIG. 17 is a block diagram of an automatic system for fertilizer application on the same field using a program developed from individual soil samples.

FIG. 17 is a representation of the application of fertilizer or pesticide, or even seeding based upon the analysis of the individual soil samples. A program for applying is developed, based on the soil analysis of each individual sample position where a sample has been taken. A vehicle fertilizer spreader 11B has an on-board computer 240 and a distance sensor 241. The distance sensor can be an odometer that would be capable of providing the locations where the soil samples were taken, when the path shown in FIG. 1 was followed. The path would be marked in some suitable manner as stated, (such as a furrow, end stakes or navigation aids) so that the vehicle 11B could follow along the previous path of the soil sampler, at each location of a soil sample. The program for applying indicated at 242 would be based upon the analysis of the soil, and can be preprogrammed into the memory for the computer 240 so that at a particular location a blend of materials from three different bins (Nitrogen, Phosphorus and Potassium) located at 244, 246 and 248 would be utilized. The bins would each have a gate or metering delivery mechanism 244A, 246A, and 248A. The gates are operated by known actuators at 244B, 246B, and 248B, respectively.

The amount of discharged material from the gate or delivery mechanism 244A, 246A, and 248A is sensed by a rate sensor of conventional design, indicated at 244C, 246C, and 248C, respectively. This information is fed back into the on-board computer at 240, and compared with the program of applying at each individual location as sensed by the distance sensor 241, and the actuators are then adjusted so that the appropriate rate is being delivered to the fertilizer spreader of nitrogen, phosphorus, and potassium, which are the bins 244, 246, and 248, respectively. The on-board adjustment can also be made in response to navigational inputs for location of a fertilizer spreader or seeder in the vehicle 11B. The path again can be followed precisely so that each grid is provided with the needed input of fertilizer or seed.

Thus, the automated soil sampler permits rapid sampling at close locations and by separately packaging and testing the soil sampler, and using that information for fertilizing at each sample, and then following the same paths with the fertilizer applicator seeder, or herbicide application, or site specific application are possible.

Although the present invention has been described with reference to preferred embodiments, workers skilled in the art will recognize that changes may be made in form and detail without departing from the spirit and scope of the invention.

What is claimed is:

1. An automatic soil sampler for providing a plurality of soil samples along a selected path of movement comprising a frame, a container on the frame, a probe assembly mounted on said frame, said probe assembly being adaptable for insertion in the soil to remove a core of soil comprising a soil sample in a first probe assembly position, a transporter for moving said probe assembly repeatedly to and from a second position adjacent the container, a packaging assembly for receiving said soil sample from the probe assembly and including a series of individual packages, each individual package receiving and soil sample from the probe assembly, a package drive for moving the individual packages in sequence in response to movement of the probe assembly to the second position; wherein said packaging assembly includes sealable sheet portions of material, said sheet portions of material merging in a bight portion, said probe assembly being positionable adjacent the bight portion for ejecting the soil sample carried thereby into the bight portion, and means for sealing the sheet portions together around the soil sample to form an individual package for each soil sample.

2. The automatic soil sampler of claim 1, and an ejector for ejecting the core of soil from the probe assembly when the packaging assembly receives each soil sample.

3. The automatic soil sampler of claim 1, wherein said probe assembly includes a probe, and means for actuating the probe from the first position to the second position in response to input signals.

4. The apparatus of claim 1 and control means for sequentially operating the probe assembly and the packaging assembly to package each soil sample in a separate package, a desired number of packages being attached to each other to form a strip of packages correlated to a sequence of soil sampling locations.

5. The automatic soil sampler of claim 2, and control means for sensing when the soil sample is ejected from the probe assembly and for actuating the packaging assembly to package the soil sample, the probe assembly being actuated in a sequence correlated to the packaging of each soil sample.

6. The automatic soil sampler of claim 1 and means for establishing the selected path of movement along a field, and for removing soil samples automatically from desired locations along the path.

7. The automatic soil sampler of claim 1, wherein said means for sealing the sheet portions of material together to form a package comprise a pair of heat sealers, means for mounting said heat sealers for movement toward and away from said sheet portions of material on opposite outer sides of the respective sheet portions, said heat sealers forming a pocket that is open toward a top of the pocket to form the bight portion for receiving a soil sample, and means for advancing the sheet portions of material to a position so that the soil sample received in the bight portion is moved below the heat sealers, said heat sealers subsequently being actuatable to seal an upper portion of the pocket in which the soil sample received in the bight portion is placed to form a sealed package.

8. The automatic soil sampler of claim 7, wherein said means for advancing the sheet portions comprise a clamp which clamps the sheet portions of material after forming the open top pocket, and for pulling the sheet portions of material after the heat sealers have been spaced from the sheet portions of material to pull the sheet portions of material through the heat sealers a desired amount.

9. The automatic soil sampler of claim 1, wherein said probe assembly is mounted on a movable probe frame including a shaft, a wheel rotatably mounted with respect to said shaft, clutch and brake means for selectively drivably engaging said wheel to drive said shaft and to hold said shaft in a desired position while said wheel rotates, said wheel being movable to a position to engage the ground, and an arm coupled to said shaft for mounting the probe assembly, and for causing the probe assembly to be inserted into the soil and removed when the wheel is coupled to the shaft and the wheel is rotating.

10. The automatic soil sampler of claim 1 and a distance measuring sensor for providing an indication of distance traveled along the path and for providing a distance signal for actuating the probe assembly.

11. The automatic soil sampler of claim 7 wherein the sheet portions of material are formed into a strip of the plurality of packages containing soil samples correlated in sequence to the sequential location of a position of sampling such soil samples along each path.

12. The apparatus of claim 1 including an indicator on the packaging assembly for identifying each package being formed from samples on the selected path of the automatic soil sampler to identify the packages relative to the position from which the soil samples were taken in the selected path.

13. The apparatus of claim 12 and a testing station for individual testing each of said soil samples for desired characteristics and for maintaining a soil sample correlation to the position from which each soil sample was taken using the indicator on said each package for the soil sample.

14. The apparatus of claim 4 and a sensor for sensing when the soil sample is moved to a position to be packaged, and for providing a signal to the control means for operating the packaging assembly.

15. An apparatus for providing individual soil samples for testing for components in the soil individually, comprising a mobile frame, a probe operable to remove a soil sample at each of a plurality of sampling locations from the soil as the mobile frame is moved along a desired path, control means to operate the probe to remove soil samples at desired intervals along the path, a soil sample packaging assembly mounted on the frame, a transport device for moving the probe to the packaging assembly, each soil sample being ejected from the probe at a location to be placed into a package formed by the packaging assembly, the packaging assembly individually packaging each of the soil samples from each sampling location, each package being correlatable to each sampling location for subsequent analysis, and wherein said packaging assembly includes a pair of sealable sheet portions of material, said sheet portions of material merging in a bight portion, said probe being positionable adjacent the bight portion for ejecting the soil sample into the bight portion, and means for sealing the sheet portions together around the soil sample received in the bight portion to form an individual package for each soil sample.

* * * * *

UNITED STATES PATENT AND TRADEMARK OFFICE
CERTIFICATE OF CORRECTION

PATENT NO.  : 5,741,983
DATED       : April 21, 1998
INVENTOR(S) : Andrey V. Skotnikov et al.

It is certified that error appears in the above-identified patent and that said Letters Patent is hereby corrected as shown below:

Claim 1, line 25, cancel "and" and insert --said--.

Signed and Sealed this

Fifteenth Day of December, 1998

Attest:

BRUCE LEHMAN

*Attesting Officer*       *Commissioner of Patents and Trademarks*